United States Patent
Cheng et al.

(10) Patent No.: US 9,034,001 B2
(45) Date of Patent: May 19, 2015

(54) SLOTTED ANCHOR DEVICE

(75) Inventors: Floria Cheng, San Francisco, CA (US); Matthew McLean, San Francisco, CA (US); Michael Wei, Redwood City, CA (US); Joseph Catanese, III, San Leandro, CA (US); Theodore C. Lamson, Pleasanton, CA (US); Earl A. Bright, II, Los Altos, CA (US)

(73) Assignee: NeoTract, Inc., Pleasanton, CA (US)

( * ) Notice: Subject to any disclaimer, the term of this patent is extended or adjusted under 35 U.S.C. 154(b) by 1047 days.

(21) Appl. No.: 12/512,731

(22) Filed: Jul. 30, 2009

(65) Prior Publication Data

US 2010/0030263 A1 Feb. 4, 2010

Related U.S. Application Data

(63) Continuation-in-part of application No. 11/775,162, filed on Jul. 9, 2007, which is a continuation-in-part of application No. 11/671,914, filed on Feb. 6, 2007, which is a continuation-in-part of application No.

(Continued)

(51) Int. Cl.
*A61B 17/08* (2006.01)
*A61B 17/04* (2006.01)
(Continued)

(52) U.S. Cl.
CPC .......... *A61B 17/0401* (2013.01); *A61B 17/0487* (2013.01); *A61B 17/0625* (2013.01); *A61B 17/32* (2013.01); *A61B 17/3468* (2013.01); *A61B 17/3478* (2013.01);
(Continued)

(58) Field of Classification Search
CPC ........... A61B 17/0401; A61B 17/0487; A61B 17/0625; A61B 17/32; A61B 17/3468
USPC ......... 606/151, 155–156, 213, 215–217, 232, 606/300, 103; 24/115 R
See application file for complete search history.

(56) References Cited

U.S. PATENT DOCUMENTS

| 659,422 A | 10/1900 | Shidler |
| 780,392 A | 1/1905 | Wanamaker et al. |

(Continued)

FOREIGN PATENT DOCUMENTS

| DE | 10159470 | 6/2003 |
| EP | 0246836 | 12/1991 |

(Continued)

OTHER PUBLICATIONS

Sharp, Howard T., M.D., et al., "Instruments and Methods—The 4-S Modification of the Roeder Knot: How to Tie It", Obstetrics & Gynecology, p. 1004-1006, vol. 90, No. 6, Dec. 1997.

(Continued)

*Primary Examiner* — Gregory Anderson

(57) ABSTRACT

A slotted anchor that secures to a connector as part of an anchor assembly is disclosed. The slotted anchor includes a pair of spaced apart prongs which join together at a slot inception. The prongs are shaped and sized of a configuration and of a rigidity to substantially prevent deflection of the prongs. The prongs include inwardly facing protrusions that are configured to capture and deform the connector between the protrusions and prevent the connector from disengaging from the slotted anchor once engaged.

15 Claims, 21 Drawing Sheets

Related U.S. Application Data

11/492,690, filed on Jul. 24, 2006, now Pat. No. 7,896,891, which is a continuation-in-part of application No. 11/318,246, filed on Dec. 22, 2005, now Pat. No. 7,645,286, which is a continuation-in-part of application No. 11/134,870, filed on May 20, 2005, now Pat. No. 7,758,594.

(60) Provisional application No. 61/084,943, filed on Jul. 30, 2008.

(51) Int. Cl.

| | | |
|---|---|---|
| A61B 17/062 | (2006.01) | |
| A61B 17/32 | (2006.01) | |
| A61B 17/34 | (2006.01) | |
| A61B 17/42 | (2006.01) | |
| A61B 17/00 | (2006.01) | |
| A61B 17/06 | (2006.01) | |
| A61B 17/068 | (2006.01) | |
| A61B 18/00 | (2006.01) | |

(52) U.S. Cl.
CPC ...... *A61B 17/42* (2013.01); *A61B 2017/00022* (2013.01); *A61B 2017/00274* (2013.01); *A61B 2017/0046* (2013.01); *A61B 2017/00792* (2013.01); *A61B 2017/00805* (2013.01); *A61B 2017/0404* (2013.01); *A61B 2017/0409* (2013.01); *A61B 2017/0417* (2013.01); *A61B 2017/0419* (2013.01); *A61B 2017/045* (2013.01); *A61B 2017/0451* (2013.01); *A61B 2017/0454* (2013.01); *A61B 2017/0464* (2013.01); *A61B 2017/0488* (2013.01); *A61B 2017/06052* (2013.01); *A61B 2017/06176* (2013.01); *A61B 2017/0688* (2013.01); *A61B 2018/00547* (2013.01)

(56) References Cited

U.S. PATENT DOCUMENTS

| | | | |
|---|---|---|---|
| 789,467 A | 5/1905 | West | |
| 2,360,164 A * | 10/1944 | Santora | 24/557 |
| 2,579,192 A | 12/1951 | Kohl | |
| 2,646,298 A | 7/1953 | Leary | |
| 2,697,624 A | 12/1954 | Thomas et al. | |
| 2,734,299 A | 2/1956 | Masson | |
| 2,825,592 A | 3/1958 | Semple | |
| 3,326,586 A | 6/1967 | Frost et al. | |
| 3,470,834 A | 10/1969 | Bone | |
| 3,521,918 A | 7/1970 | Hammond | |
| 3,713,680 A | 1/1973 | Pagano | |
| 3,716,058 A | 2/1973 | Tanner, Jr. | |
| 3,756,638 A | 9/1973 | Stockberger | |
| 3,873,140 A | 3/1975 | Bloch | |
| 3,875,648 A | 4/1975 | Bone | |
| 3,931,667 A | 1/1976 | Merser et al. | |
| 3,976,079 A | 8/1976 | Samuels et al. | |
| 4,006,747 A | 2/1977 | Kronenthal et al. | |
| 4,210,148 A | 7/1980 | Stivala | |
| 4,235,238 A | 11/1980 | Ogiu et al. | |
| 4,291,698 A | 9/1981 | Fuchs et al. | |
| 4,409,974 A | 10/1983 | Freedland | |
| 4,493,323 A | 1/1985 | Albright et al. | |
| 4,513,746 A | 4/1985 | Aranyi | |
| 4,621,640 A | 11/1986 | Mulhollan et al. | |
| 4,657,461 A | 4/1987 | Smith | |
| 4,669,473 A | 6/1987 | Richards et al. | |
| 4,705,040 A | 11/1987 | Mueller et al. | |
| 4,714,281 A | 12/1987 | Peck | |
| 4,738,255 A | 4/1988 | Goble et al. | |
| 4,741,330 A | 5/1988 | Hayhurst | |
| 4,744,364 A | 5/1988 | Kensey | |
| 4,750,492 A | 6/1988 | Jacobs | |
| 4,762,128 A | 8/1988 | Rosenbluth | |
| 4,823,794 A | 4/1989 | Pierce | |
| 4,899,743 A | 2/1990 | Nicholson et al. | |
| 4,926,860 A | 5/1990 | Stice | |
| 4,946,468 A | 8/1990 | Li | |
| 4,955,913 A | 9/1990 | Robinson | |
| 4,968,315 A | 11/1990 | Gatturna et al. | |
| 5,002,550 A | 3/1991 | Li | |
| 5,041,129 A | 8/1991 | Hayhurst et al. | |
| 5,046,513 A | 9/1991 | Gatturna et al. | |
| 5,053,046 A | 10/1991 | Janese | |
| 5,100,421 A | 3/1992 | Christoudias | |
| 5,123,914 A | 6/1992 | Cope | |
| 5,129,912 A | 7/1992 | Noda et al. | |
| 5,192,303 A | 3/1993 | Gatturna et al. | |
| 5,203,787 A | 4/1993 | Noblitt et al. | |
| 5,217,470 A | 6/1993 | Weston | |
| 5,217,486 A | 6/1993 | Rice et al. | |
| 5,234,454 A | 8/1993 | Bangs | |
| 5,236,445 A | 8/1993 | Hayhurst et al. | |
| 5,258,015 A | 11/1993 | Li et al. | |
| 5,269,809 A | 12/1993 | Hayhurst et al. | |
| 5,330,488 A | 7/1994 | Goldrath | |
| 5,334,200 A | 8/1994 | Johnson | |
| 5,336,240 A | 8/1994 | Metzler et al. | |
| 5,354,271 A | 10/1994 | Voda | |
| 5,358,511 A | 10/1994 | Gatturna et al. | |
| 5,364,408 A | 11/1994 | Gordon | |
| 5,366,490 A | 11/1994 | Edwards et al. | |
| 5,368,599 A | 11/1994 | Hirsch et al. | |
| 5,370,646 A | 12/1994 | Reese et al. | |
| 5,380,334 A | 1/1995 | Torrie et al. | |
| 5,391,182 A | 2/1995 | Chin | |
| 5,403,348 A | 4/1995 | Bonutti | |
| 5,405,352 A | 4/1995 | Weston | |
| 5,411,520 A | 5/1995 | Nash et al. | |
| 5,417,691 A | 5/1995 | Hayhurst | |
| 5,435,805 A | 7/1995 | Edwards et al. | |
| 5,470,337 A | 11/1995 | Moss | |
| 5,472,446 A | 12/1995 | de la Torre | |
| 5,480,406 A | 1/1996 | Nolan et al. | |
| 5,501,690 A | 3/1996 | Measamer et al. | |
| 5,507,754 A | 4/1996 | Green et al. | |
| 5,522,846 A | 6/1996 | Bonutti | |
| 5,531,763 A | 7/1996 | Mastri et al. | |
| 5,536,240 A | 7/1996 | Edwards et al. | |
| 5,540,704 A | 7/1996 | Gordon et al. | |
| 5,545,171 A | 8/1996 | Sharkey et al. | |
| 5,545,178 A | 8/1996 | Kensey et al. | |
| 5,550,172 A | 8/1996 | Regula et al. | |
| 5,554,162 A | 9/1996 | DeLange | |
| 5,554,171 A | 9/1996 | Gatturna et al. | |
| 5,562,689 A | 10/1996 | Green et al. | |
| 5,569,305 A | 10/1996 | Bonutti | |
| 5,571,104 A | 11/1996 | Li | |
| 5,573,540 A | 11/1996 | Yoon | |
| 5,578,044 A | 11/1996 | Gordon et al. | |
| 5,591,177 A | 1/1997 | Lehrer | |
| 5,593,421 A | 1/1997 | Bauer | |
| 5,611,515 A | 3/1997 | Benderev et al. | |
| 5,626,614 A | 5/1997 | Hart | |
| 5,630,824 A | 5/1997 | Hart | |
| 5,647,836 A | 7/1997 | Blake, III et al. | |
| 5,665,109 A | 9/1997 | Yoon | |
| 5,667,486 A | 9/1997 | Mikulich et al. | |
| 5,669,917 A | 9/1997 | Sauer et al. | |
| 5,690,649 A | 11/1997 | Li | |
| 5,690,677 A | 11/1997 | Schmieding et al. | |
| 5,697,950 A | 12/1997 | Fucci et al. | |
| 5,707,394 A | 1/1998 | Miller et al. | |
| 5,716,368 A | 2/1998 | de la Torre et al. | |
| 5,718,717 A | 2/1998 | Bonutti | |
| 5,725,556 A | 3/1998 | Moser et al. | |
| 5,725,557 A | 3/1998 | Gatturna et al. | |
| 5,733,306 A | 3/1998 | Bonutti | |
| 5,741,276 A | 4/1998 | Poloyko et al. | |
| 5,746,753 A | 5/1998 | Sullivan et al. | |
| 5,749,846 A | 5/1998 | Edwards et al. | |
| 5,752,963 A | 5/1998 | Allard et al. | |

(56) References Cited

U.S. PATENT DOCUMENTS

| | | |
|---|---|---|
| 5,782,862 A | 7/1998 | Bonutti |
| 5,782,864 A | 7/1998 | Lizardi |
| 5,791,022 A * | 8/1998 | Bohman ............... 24/130 |
| 5,800,445 A | 9/1998 | Ratcliff et al. |
| 5,807,403 A | 9/1998 | Beyar et al. |
| 5,810,848 A | 9/1998 | Hayhurst |
| 5,814,072 A | 9/1998 | Bonutti |
| 5,830,221 A | 11/1998 | Stein |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,897,574 A | 4/1999 | Bonutti |
| 5,899,911 A | 5/1999 | Carter |
| 5,899,921 A | 5/1999 | Caspari et al. |
| 5,904,696 A | 5/1999 | Rosenman |
| 5,908,428 A | 6/1999 | Scirica et al. |
| 5,919,198 A | 7/1999 | Graves, Jr. et al. |
| 5,919,202 A | 7/1999 | Yoon |
| 5,921,986 A | 7/1999 | Bonutti |
| 5,928,252 A | 7/1999 | Steadman et al. |
| 5,931,844 A | 8/1999 | Thompson et al. |
| 5,944,739 A | 8/1999 | Zlock et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Wilard |
| 5,971,447 A | 10/1999 | Steck, III |
| 6,010,514 A | 1/2000 | Burney et al. |
| 6,011,525 A | 1/2000 | Piole |
| 6,015,428 A * | 1/2000 | Pagedas ............... 606/232 |
| 6,030,393 A | 2/2000 | Corlew |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,056,722 A | 5/2000 | Jayaraman |
| 6,056,772 A | 5/2000 | Bonutti |
| 6,066,160 A * | 5/2000 | Colvin et al. ............... 606/232 |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,160 A | 9/2000 | Bonutti |
| 6,117,161 A | 9/2000 | Li et al. |
| 6,120,539 A | 9/2000 | Eldridge et al. |
| 6,139,555 A | 10/2000 | Hart et al. |
| RE36,974 E | 11/2000 | Bonutti |
| 6,143,006 A | 11/2000 | Chan |
| 6,159,234 A | 12/2000 | Bonutti et al. |
| 6,200,329 B1 | 3/2001 | Fung et al. |
| 6,206,895 B1 | 3/2001 | Levinson |
| 6,228,096 B1 | 5/2001 | Marchand |
| 6,258,124 B1 | 7/2001 | Darois et al. |
| 6,261,302 B1 | 7/2001 | Voegele et al. |
| 6,270,530 B1 | 8/2001 | Eldridge et al. |
| 6,280,460 B1 | 8/2001 | Bolduc et al. |
| 6,290,711 B1 | 9/2001 | Caspari et al. |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,398,795 B1 | 6/2002 | McAlister et al. |
| 6,425,900 B1 | 7/2002 | Knodel et al. |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,195 B2 | 12/2002 | Bonutti |
| 6,506,190 B1 | 1/2003 | Walshe |
| 6,506,196 B1 | 1/2003 | Laufer |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,592,609 B1 | 7/2003 | Bonutti |
| 6,596,013 B2 | 7/2003 | Yang et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | St. Goar et al. |
| 6,641,592 B1 | 11/2003 | Sauer et al. |
| 6,656,182 B1 | 12/2003 | Hayhurst |
| 6,660,023 B2 | 12/2003 | McDevitt et al. |
| 6,663,589 B1 | 12/2003 | Halevy |
| 6,663,639 B1 | 12/2003 | Laufer et al. |
| 6,699,263 B2 | 3/2004 | Cope |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom, Jr. |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Neisz et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,011,688 B2 | 3/2006 | Gryska et al. |
| 7,015,253 B2 | 3/2006 | Escandon et al. |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,105,004 B2 | 9/2006 | Dicesare et al. |
| 7,108,655 B2 | 9/2006 | Whalen et al. |
| 7,141,038 B2 | 11/2006 | Whalen et al. |
| 7,153,314 B2 | 12/2006 | Laufer et al. |
| 7,179,225 B2 | 2/2007 | Shluzas |
| 7,226,558 B2 | 6/2007 | Nieman et al. |
| 7,232,448 B2 | 6/2007 | Battles et al. |
| 7,288,063 B2 | 10/2007 | Petros et al. |
| 7,303,108 B2 | 12/2007 | Shelton, IV |
| 7,320,701 B2 | 1/2008 | Haut et al. |
| 7,322,974 B2 | 1/2008 | Swoyer et al. |
| 7,334,822 B1 | 2/2008 | Hines, Jr. |
| 7,340,300 B2 | 3/2008 | Christopherson et al. |
| 7,399,304 B2 | 7/2008 | Gambale et al. |
| 7,402,166 B2 | 7/2008 | Feigl |

(56) References Cited

U.S. PATENT DOCUMENTS

| | | |
|---|---|---|
| 7,416,554 B2 | 8/2008 | Lam et al. |
| 7,553,317 B2 | 6/2009 | Weisenburgh, II et al. |
| 7,608,108 B2 | 10/2009 | Bhatnagar et al. |
| 7,658,311 B2 | 2/2010 | Boudreaux |
| 7,674,275 B2 | 3/2010 | Martin et al. |
| 7,727,248 B2 | 6/2010 | Smith et al. |
| 2001/0044639 A1 | 11/2001 | Levinson |
| 2002/0095154 A1 | 7/2002 | Atkinson et al. |
| 2002/0128684 A1 | 9/2002 | Foerster |
| 2002/0161382 A1 | 10/2002 | Neisz et al. |
| 2002/0193809 A1 | 12/2002 | Meade |
| 2003/0109769 A1 | 6/2003 | Lowery et al. |
| 2003/0191497 A1 | 10/2003 | Cope |
| 2003/0204195 A1 | 10/2003 | Keane et al. |
| 2003/0236535 A1* | 12/2003 | Onuki et al. .................. 606/144 |
| 2004/0030217 A1 | 2/2004 | Yeung et al. |
| 2004/0043052 A1 | 3/2004 | Hunter et al. |
| 2004/0078046 A1 | 4/2004 | Barzell et al. |
| 2004/0193191 A1 | 9/2004 | Starksen et al. |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0243227 A1 | 12/2004 | Starksen et al. |
| 2004/0260345 A1 | 12/2004 | Foerster |
| 2005/0055087 A1 | 3/2005 | Starksen |
| 2005/0065550 A1 | 3/2005 | Starksen et al. |
| 2005/0107811 A1 | 5/2005 | Starksen et al. |
| 2005/0107812 A1 | 5/2005 | Starksen et al. |
| 2005/0154401 A1 | 7/2005 | Weldon et al. |
| 2005/0177181 A1 | 8/2005 | Kagan et al. |
| 2005/0203344 A1 | 9/2005 | Orban, III et al. |
| 2005/0203550 A1 | 9/2005 | Laufer et al. |
| 2005/0216078 A1 | 9/2005 | Starksen et al. |
| 2005/0267405 A1 | 12/2005 | Shah |
| 2005/0273138 A1 | 12/2005 | Starksen et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0058817 A1 | 3/2006 | Starksen et al. |
| 2006/0089646 A1 | 4/2006 | Bonutti |
| 2006/0167477 A1 | 7/2006 | Arcia et al. |
| 2006/0241694 A1* | 10/2006 | Cerundolo ................. 606/232 |
| 2006/0265042 A1 | 11/2006 | Catanese, III et al. |
| 2006/0282081 A1 | 12/2006 | Fanton et al. |
| 2007/0049929 A1 | 3/2007 | Catanese, III |
| 2007/0049970 A1 | 3/2007 | Belef et al. |
| 2007/0060931 A1 | 3/2007 | Hamilton et al. |
| 2007/0088362 A1 | 4/2007 | Bonutti |
| 2007/0112385 A1 | 5/2007 | Conlon |
| 2007/0142846 A1 | 6/2007 | Catanese |
| 2007/0173888 A1 | 7/2007 | Gertner et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0033488 A1 | 2/2008 | Catanese, III et al. |
| 2008/0039894 A1 | 2/2008 | Catanese, III et al. |
| 2008/0045978 A1 | 2/2008 | Kuhns et al. |
| 2008/0058710 A1 | 3/2008 | Wilk |
| 2008/0065120 A1 | 3/2008 | Zannis |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0195145 A1 | 8/2008 | Bonutti et al. |
| 2008/0208220 A1 | 8/2008 | Shiono et al. |
| 2010/0010631 A1 | 1/2010 | Otte et al. |
| 2010/0114162 A1 | 5/2010 | Bojarski et al. |
| 2010/0286106 A1 | 11/2010 | Gat et al. |
| 2010/0286679 A1 | 11/2010 | Hoey et al. |

FOREIGN PATENT DOCUMENTS

| | | |
|---|---|---|
| EP | 0464480 | 1/1992 |
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| JP | 9122134 | 5/1997 |
| JP | 2004344427 | 12/2004 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO9210142 | 6/1992 |
| WO | WO9304727 | 3/1993 |
| WO | WO9315664 | 8/1993 |
| WO | WO0230335 | 4/2002 |
| WO | WO03039334 | 5/2003 |
| WO | WO03077772 | 9/2003 |
| WO | WO-2004017845 | 3/2004 |
| WO | WO2004017845 | 3/2004 |
| WO | WO2004019787 | 3/2004 |
| WO | WO2004030569 | 4/2004 |
| WO | WO2004103189 | 12/2004 |
| WO | WO-2007053516 | 5/2007 |
| WO | WO2007053516 | 5/2007 |
| WO | WO2007064906 | 6/2007 |
| WO | WO2008006084 | 1/2008 |
| WO | WO2008043044 | 4/2008 |
| WO | WO2008043917 | 4/2008 |
| WO | WO2009009617 | 1/2009 |
| WO | WO2010011832 | 1/2010 |

OTHER PUBLICATIONS

P. Schauer et al., "New applications for endoscopy: the emerging field of endoluminal and transgastric bariatric surgery," Surgical Endoscopy, Received Apr. 24, 2006/Accepted Jun. 7, 2006.

PCT search report dated Oct. 9, 2009 for PCT application No. PCT/US2009/052275 as issued by the European Patent Office as searching authority.

Richard Berges et al., "Alternative Minimalinvasive Therapien Beim Benignen Prostatasyndrom", medizin, Jg, 104 heft 37, Sep. 14, 2007.

Rudolf Hartung, et al., Instrumentelle Therapie der benegnen Prostatahyperplasie, Medizin, Deutsches Arzteblatt 97, Heft 15, Apr. 14, 2000.

Klaus Hofner, et al., "Operative Therapie des benignen Prostatasyndroms", Medizin, Dtsch Arztebl 2007; 194(36): A2424-9.

R. Hubmann, Geschichte der transurethralen Prostataeingriffe, Geschichte der Medizin, Urologe [B} 2000 40: 152-160.

U. Jonas, et al. Benigne Prostatahyperplasie, Der Urologe 2006, [Sonderheft] 45: 134-144.

O.A. Bacharova, et al. "The Effect of *Rhodiolae rosea* Extract on Incidence Rate of Superficial Bladder Carcinoma Relapses", Kozin 1995.

S. Kruck, et al., "Aktuelle Therapiemoglichkeiten des Benignen Prostata-Syndroms", J Urol Urogynakol 209; 16 (1): 19-22, 2009.

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstruction in Male", Pharma Medica vol. 8 No. 8, p. 35-39, 1990.

O. Reich, et al., "Benignes Prostatasyndrom (BPS)", er Urologe A Issue vol. 45, No. 6, Jun. 2006, p. 769-782.

(56) References Cited

OTHER PUBLICATIONS

Daito Takashi, "Low-Invasive Treatment for BPH", Medico vol. 34, No. 10 p. 366-369, Date Unknown.

Trapeznikov et al., "New Technologies in the Treatment of Benign Prostatic Hyperplasia", Urologia Nefrol (Mosk), Jul.-Aug. 1996 (4): 41-47.

Koyanagi Tomohiko, et al., "Surgery View of 21st Century", Urological Surgery, vol. 84, No. 1 p. 47-53, 2001.

Borzhievski et al., "Tactics of the Surgical Treatment of Patients With Prostatic Adenoma and Acute Urinary Retention", Urologia Nefrol (Mosk). Jan.-Feb. 1987, (1): 39-43.

Yeung, Jeff, "Treating Urinary Stress Incontinence Without Incision with Endoscopic Suture Anchor & Approximating Device," Aleeva Medical, Inc., 2007.

European Application Serial No. 09791011.1, European Office Action mailed Jul. 25, 2014, 5 pgs.

\* cited by examiner

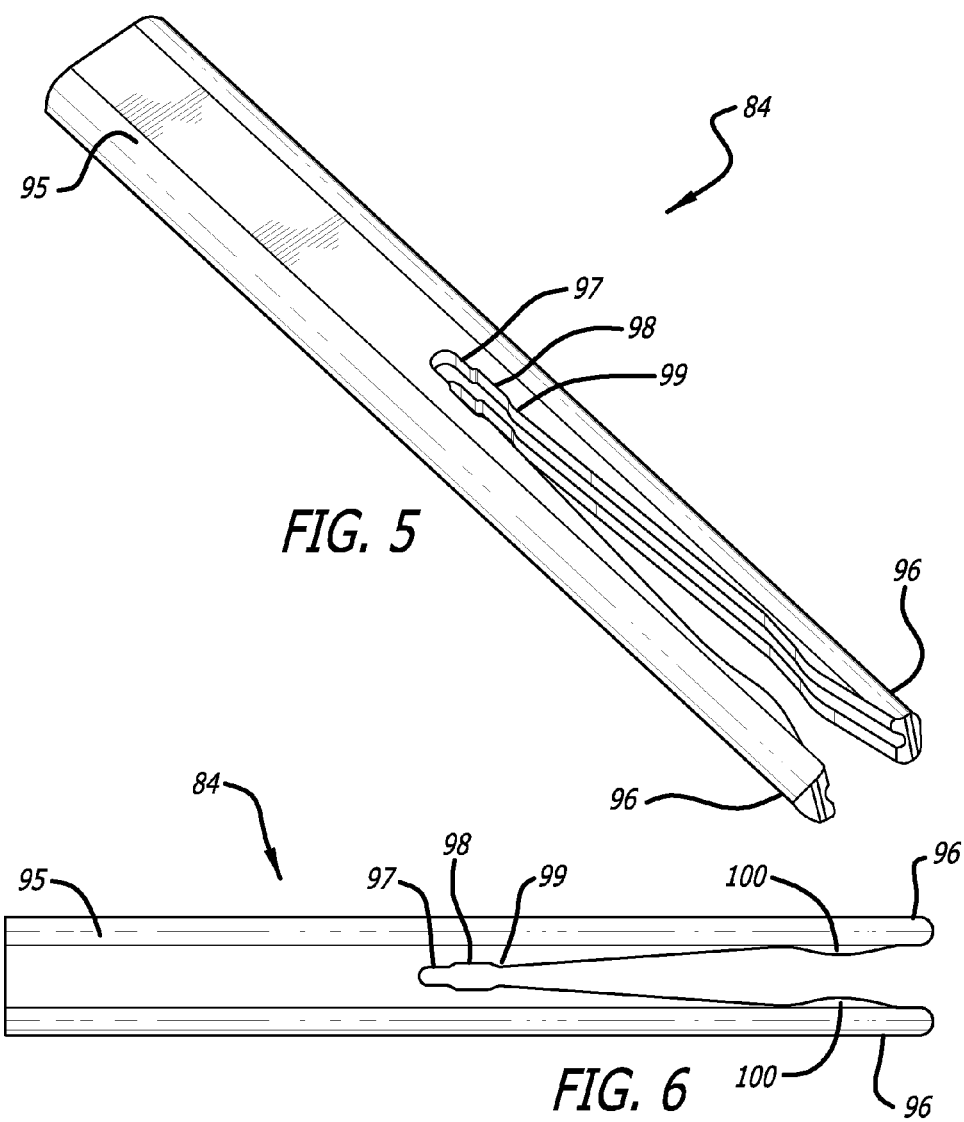
FIG. 5
FIG. 6
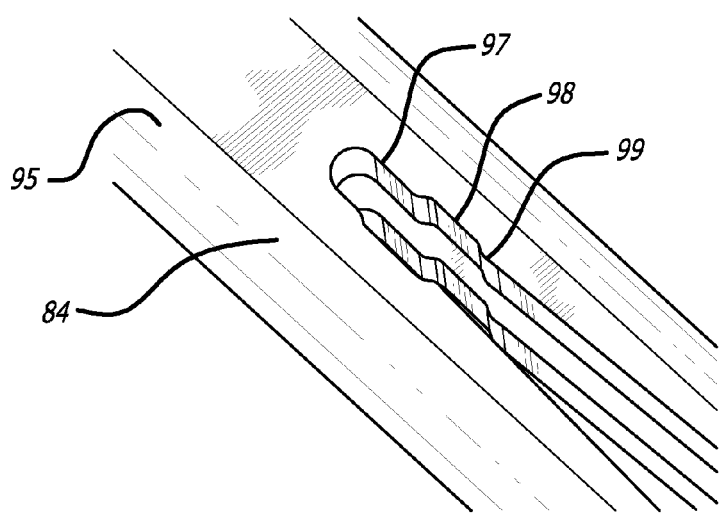
FIG. 7

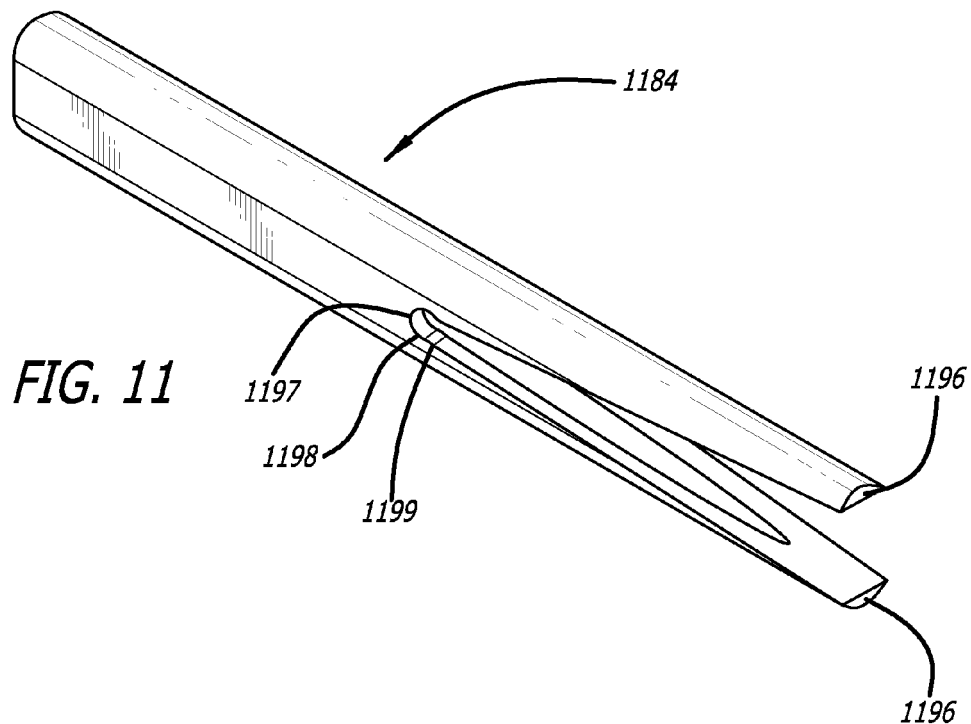
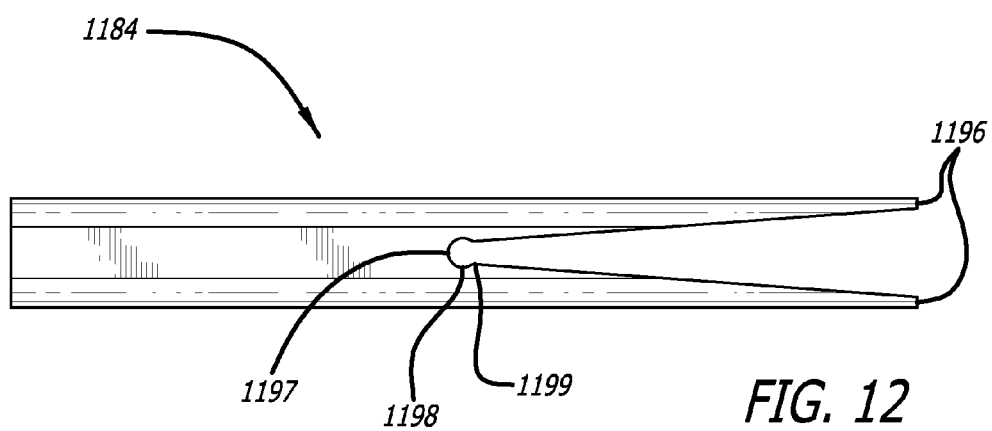

SLOTTED ANCHOR DEVICE

CROSS-REFERENCE TO RELATED APPLICATIONS

This application is a continuation-in-part of copending U.S. patent application Ser. No. 11/775,162 entitled Multi-Actuating Trigger Anchor Delivery System, filed Jul. 9, 2007, which is a continuation-in-part of copending U.S. patent application Ser. No. 11/671,914, entitled Integrated Handle Assembly For Anchor Delivery System, filed Feb. 6, 2007, which is a continuation-in-part of copending U.S. patent application Ser. No. 11/492,690, entitled Apparatus and Method for Manipulating or Retracting Tissue and Anatomical Structure, filed on Jul. 24, 2006, which is a continuation-in-part of copending U.S. patent application Ser. No. 11/318,246, entitled Devices, Systems and Methods for Retracting, Lifting, Compressing, Supporting or Repositioning Tissues or Anatomical Structures, filed on Dec. 22, 2005, which is a continuation-in-part of copending U.S. patent application Ser. No. 11/134,870 entitled Devices, Systems and Methods for Treating Benign Prostatic Hyperplasia and Other Conditions, filed on May 20, 2005, the entire disclosures of which are expressly incorporated herein by reference and claims the benefit of Provisional Application Ser. Nos. 61/084,937 61/084,943.

FIELD OF THE INVENTION

The disclosed embodiments relate generally to medical devices and methods, and more particularly to systems and associated methods for manipulating or retracting tissues and anatomical or other structures within the body of human or animal subjects for the purpose of treating diseases or disorders.

BACKGROUND

There are a wide variety of situations in which it is desirable to lift, compress or otherwise reposition normal or aberrant tissues or anatomical structures (e.g., glands, organs, ligaments, tendons, muscles, tumors, cysts, fat pads, and the like) within the body of a human or animal subject. Such procedures are often carried out for the purpose of treating or palliating the effects of diseases or disorders (e.g., hyperplasic conditions, hypertrophic conditions, neoplasias, prolapses, herniations, stenoses, constrictions, compressions, transpositions, congenital malformations, and the like) and/or for cosmetic purposes (e.g., face lifts, breast lifts, brow lifts, and the like) and/or for research and development purposes (e.g., to create animal models that mimic various pathological conditions). In many of these procedures, surgical incisions are made in the body, and laborious surgical dissection is performed to access and expose the affected tissues or anatomical structures. Thereafter, in some cases, the affected tissues or anatomical structures are removed or excised. In other cases, various natural or man-made materials are used to lift, sling, reposition or compress the affected tissues.

Benign Prostatic Hyperplasia (BPH):

One example of a condition where it is desirable to lift, compress or otherwise remove a pathologically enlarged tissue is Benign Prostatic Hyperplasia (BPH). BPH is one of the most common medical conditions that affects men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH is expected to increase as the average age of the population increases in developed countries.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus, the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate, and the like.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine, and the like) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Medications for treating BPH symptoms include phytotherapy and prescription medications. In phytotherapy, plant products such as Saw Palmetto, African Pygeum, Serenoa Repens (sago palm) and South African star grass are administered to the patient. Prescription medications are prescribed as first line therapy in patients with symptoms that are interfering with their daily activities. Two main classes of prescription medications are alpha-1 a-adrenergic receptors blockers and 5-alpha-reductase inhibitors. Alpha-1 a-adrenergic receptors blockers block the activity of alpha-1 a-adrenergic receptors that are responsible for causing constriction of smooth muscle cells in the prostate. Thus, blocking the activity of alpha-1 a-adrenergic receptors causes prostatic smooth muscle relaxation. This, in turn, reduces urethral resistance thereby reducing the severity of the symptoms. 5-alpha-reductase inhibitors block the conversion of testosterone to di-hydro-testosterone. Di-hydro-testosterone causes growth of epithelial cells in the prostate gland. Thus, 5-alpha-reductase inhibitors cause regression of epithelial cells in the prostate gland and, hence, reduce the volume of the prostate gland, which in turn reduces the severity of the symptoms.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Transurethal Resection of Prostate (TURP) is the most commonly practiced surgical procedure implemented for the treatment of BPH. In this procedure, prostatic urethral obstruction is reduced by removing most of the prostatic urethra and a sizeable volume of the surrounding prostate gland. This is carried out under general or spinal anesthesia. In this procedure, a urologist visualizes the urethra by inserting a resectoscope, that houses an optical lens in communication with a video camera, into the urethra such that the distal region of the resectoscope is in the region of the urethra surrounded by the prostate gland. The distal region of the resectoscope consists of an electric cutting loop that can cut prostatic tissue when an electric current is applied to the device. An electric return pad is placed on the patient to close the cutting circuit. The electric cutting loop is used to scrape away tissue from the inside of the prostate gland. The tissue that is scraped away is flushed out of the urinary system using an irrigation fluid. Using a coagulation energy setting, the loop is also used to cauterize transected vessels during the operation.

Another example of a surgical procedure for treating BPH symptoms is Transurethral Electrovaporization of the Prostate (TVP). In this procedure, a part of prostatic tissue squeezing the urethra is desiccated or vaporized. This is carried out under general or spinal anesthesia. In this procedure, a resectoscope is inserted transurethrally such that the distal region of the resectoscope is in the region of the urethra surrounded by the prostate gland. The distal region of the resectoscope consists of a rollerball or a grooved roller electrode. A controlled amount of electric current is passed through the electrode. The surrounding tissue is rapidly heated up and vaporized to create a vaporized space. Thus, the region of the urethra that is blocked by the surrounding prostate gland is opened up.

Another example of a surgical procedure for treating BPH symptoms is Transurethral Incision of the Prostate (TUIP). In this procedure, the resistance to urine flow is reduced by making one or more incisions in the prostate gland in the region where the urethra meets the urinary bladder. This procedure is performed under general or spinal anesthesia. In this procedure, one or more incisions are made in the muscle of the bladder neck, which is the region where the urethra meets the urinary bladder. The incisions are in most cases deep enough to cut the surrounding prostate gland tissue including the prostatic capsule. This releases any compression on the bladder neck and causes the bladder neck to spring apart. The incisions can be made using a resectoscope, laser beam, and the like.

Another example of a surgical procedure for treating BPH symptoms is Laser Prostatectomy. Two common techniques used for Laser Prostatectomy are Visual Laser Ablation of the Prostate (VLAP) and the Holmium Laser Resection/Enucleation of the Prostate (HoLEP). In VLAP, a neodymium: Yttrium-aluminum-garnet (NdYAG) laser is used to ablate tissue by causing coagulation necrosis. The procedure is performed under visual guidance. In HoLEP, a holmium: Yttrium-aluminum-garnet laser is used for direct contact ablation of tissue. Both these techniques are used to remove tissue obstructing the urethral passage to reduce the severity of BPH symptoms.

Another example of a surgical procedure for treating BPH symptoms is Photoselective Vaporization of the Prostate (PVP). In this procedure, laser energy is used to vaporize prostatic tissue to relieve obstruction to urine flow in the urethra. The type of laser used is the Potassium-Titanyl-Phosphate (KTP) laser. The wavelength of this laser is highly absorbed by oxyhemoglobin. This laser vaporizes cellular water and, hence, is used to remove tissue that is obstructing the urethra.

Another example of a surgical procedure for treating BPH symptoms is Open Prostatectomy. In this procedure, the prostate gland is surgically removed by an open surgery. This is done under general anesthesia. The prostate gland is removed through an incision in the lower abdomen or the perineum. The procedure is used mostly in patients that have a large (greater than approximately 100 grams) prostate gland.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

In Transurethral Microwave Thermotherapy (TUMT), microwave energy is used to generate heat that destroys hyperplastic prostate tissue. This procedure is performed under local anesthesia. In this procedure, a microwave antenna is inserted in the urethra. A rectal thermosensing unit is inserted into the rectum to measure rectal temperature. Rectal temperature measurements are used to prevent overheating of the anatomical region. The microwave antenna is then used to deliver microwaves to lateral lobes of the prostate gland. The microwaves are absorbed as they pass through prostate tissue. This generates heat which in turn destroys the prostate tissue. The destruction of prostate tissue reduces the degree of squeezing of the urethra by the prostate gland, thus, reducing the severity of BPH symptoms.

Another example of a minimally invasive procedure for treating BPH symptoms is Transurethral Needle Ablation (TUNA). In this procedure, heat-induced coagulation necrosis of prostate tissue regions causes the prostate gland to shrink. It is performed using local anesthetic and intravenous or oral sedation. In this procedure, a delivery catheter is inserted into the urethra. The delivery catheter comprises two radiofrequency needles that emerge at an angle of 90 degrees from the delivery catheter. The two radiofrequency needles are aligned at an angle of 40 degrees to each other so that they penetrate the lateral lobes of the prostate. A radiofrequency current is delivered through the radiofrequency needles to heat the tissue of the lateral lobes to 70-100 degree Celsius at a radiofrequency power of approximately 456 KHz for approximately 4 minutes per lesion. This creates coagulation defects in the lateral lobes. The coagulation defects cause shrinkage of prostatic tissue which in turn reduces the degree of squeezing of the urethra by the prostate gland thus reducing the severity of BPH symptoms.

Another example of a minimally invasive procedure for treating BPH symptoms is Interstitial Laser Coagulation (ILC). In this procedure, laser-induced necrosis of prostate tissue regions causes the prostate gland to shrink. It is performed using regional anesthesia, spinal or epidural anesthesia or local anesthesia (periprostatic block). In this procedure, a cystoscope sheath is inserted into the urethra, and the region of the urethra surrounded by the prostate gland is inspected. A laser fiber is inserted into the urethra. The laser fiber has a sharp distal tip to facilitate the penetration of the laser scope into prostatic tissue. The distal tip of the laser fiber has a distal-diffusing region that distributes laser energy 360° along the terminal 3 mm of the laser fiber. The distal tip is inserted into the middle lobe of the prostate gland, and laser energy is delivered through the distal tip for a desired time. This heats the middle lobe and causes laser-induced necrosis of the tissue around the distal tip. Thereafter, the distal tip is withdrawn from the middle lobe. The same procedure of inserting the distal tip into a lobe and delivering laser energy is repeated with the lateral lobes. This causes tissue necrosis in several regions of the prostate gland which, in turn, causes the prostate gland to shrink. Shrinkage of the prostate gland reduces the degree of squeezing of the urethra by the prostate, thus, reducing the severity of BPH symptoms.

Another example of a minimally invasive procedure for treating BPH symptoms is implanting Prostatic Stents. In this procedure, the region of urethra surrounded by the prostate is mechanically supported to reduce the constriction caused by an enlarged prostate. Prostatic stents are flexible devices that are expanded after their insertion in the urethra. They mechanically support the urethra by pushing the obstructing prostatic tissue away from the urethra. This reduces the constriction of the urethra and improves urine flow past the prostate gland thereby reducing the severity of BPH symptoms.

Although existing treatments provide some relief to the patient from symptoms of BPH, they have disadvantages. Alpha-1 a-adrenergic receptors blockers have side effects such as dizziness, postural hypotension, lightheadedness, asthenia and nasal stuffiness. Retrograde ejaculation can also occur. 5-alpha-reductase inhibitors have minimal side effects, but only have a modest effect on BPH symptoms and the flow rate of urine. In addition, anti-androgens, such as 5-alpha-reductase, require months of therapy before LUTS improvements are observed. Surgical treatments of BPH carry a risk of complications including erectile dysfunction; retrograde ejaculation; urinary incontinence; complications related to anesthesia; damage to the penis or urethra; need for a repeat surgery; and the like. Even TURP, which is the gold standard in treatment of BPH, carries a high risk of complications. Adverse events associated with this procedure are reported to include retrograde ejaculation (65% of patients), post-operative irritation (15%), erectile dysfunction (10%), need for transfusion (8%), bladder neck constriction (7%), infection (6%), significant hematuria (6%), acute urinary retention (5%), need for secondary procedure (5%), and incontinence (3%). Typical recovery from TURP involves several days of inpatient hospital treatment with an indwelling urethral catheter, followed by several weeks in which obstructive symptoms are relieved, but there is pain or discomfort during micturition.

The reduction in the symptom score after minimally invasive procedures is not as large as the reduction in symptom score after TURP. Up to 25% of patients who receive these minimally invasive procedures ultimately undergo a TURP within 2 years. The improvement in the symptom score generally does not occur immediately after the procedure. For example, it takes an average of one month for a patient to notice improvement in symptoms after TUMT and 1.5 months to notice improvement after ILC. In fact, symptoms are typically worse for these therapies that heat or cook tissue, because of the swelling and necrosis that occurs in the initial weeks following the procedures. Prostatic stents often offer more immediate relief from obstruction but are now rarely used because of high adverse effect rates. Stents have the risk of migration from the original implant site (up to 12.5% of patients), encrustation (up to 27.5%), incontinence (up to 3%), and recurrent pain and discomfort. In published studies, these adverse effects necessitated 8% to 47% of stents to be explanted. Overgrowth of tissue through the stent and complex stent geometries has made their removal quite difficult and invasive.

Thus, the most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and, in fact, often experiences worse symptoms for weeks after the procedure until the body begins to heal. Additionally, all device approaches require a urethral catheter placed in the bladder, and in some cases for weeks. In some cases, catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

Cosmetic or Reconstructive Tissue Lifting and Repositioning:

Many cosmetic or reconstructive surgical procedures involve lifting, compressing or repositioning of natural tissue, natural tissue or artificial grafts, or aberrant tissue. For example, surgical procedures such as face lifts, brow lifts, neck lifts, tummy tucks, and the like, have become commonplace. In many cases, these procedures are performed by creating incisions through the skin, dissecting to a plane beneath muscles and fascia, freeing the muscles, fascia and overlying skin from underlying structures (e.g., bone or other muscles), lifting or repositioning the freed muscles, fascia and overlying skin, and then attaching the repositioned tissues to underlying or nearby structures (e.g., bone, periostium, or other muscles) to hold the repositioned tissues in their new (e.g., lifted) position. In some cases, excess skin may also be removed during the procedure.

There have been attempts to develop minimally invasive devices and methods for cosmetic lifting and repositioning of tissues. For example, connector suspension lifts have been developed where one end of a standard or modified connector thread is attached to muscle and the other end is anchored to bone, periostium or another structure to lift and reposition the tissues as desired. Some of these connector suspension techniques have been performed through cannulas or needles inserted though relatively small incisions of puncture wounds.

There remains a need for the development of a suture lock or suture anchor that can be used throughout the body The disclosed embodiments address these and other needs.

SUMMARY

Briefly and in general terms, the present disclosure is directed towards a slotted suture anchor which includes a back end that resembles a flattened tube in shape, with a width in lateral cross-section that is greater than its thickness. The slotted suture anchor also includes a pair of spaced apart prongs. The spaced prongs join together at a slot inception. The prongs are shaped and sized of a configuration and of a rigidity to substantially prevent deflection of the prongs. The mechanism of suture attachment and strength of the assembly is a combination of compression of the suture between the stiff slotted prongs of the anchor as well as disruption of the suture surface by the discreet edges of the slotted, flattened-tubular anchor. The discreet edges provide a lower contact surface area between anchor prongs and suture and focuses the compressive forces in focal points that cause the suture to conform around both internal recesses and external faces. In some embodiments, the prongs include inwardly facing protrusions that are configured to capture and deform the suture between the protrusions and prevent the suture from disengaging from the slotted anchor device once engaged.

Various further embodiments of slotted anchors are also contemplated. In each, a pair of rigid prongs are provided so that a grip onto a connector can be achieved without the necessity or significant reliance upon an additional locking member. In particular, various embodiments of slotted structures are disclosed which accordingly provide alternative approaches to inward extending protrusions as well as the slot inception of the device.

Other features and advantages will become apparent from the following detailed description, taken in conjunction with the accompanying drawings, which illustrate by way of example, the features of the various embodiments.

BRIEF DESCRIPTION OF THE DRAWINGS

FIG. 5 is a perspective view of another embodiment of a slotted anchor;

FIG. 6 is top view of the slotted anchor of FIG. 5;

FIG. 7 is a close up perspective view of the slot inception, wider seating region, and inwardly facing protrusions of the slotted anchor of FIG. 5;

FIG. 11 is a perspective view of a slotted anchor;

FIG. 12 is a top view of the slotted anchor of FIG. 11;

DETAILED DESCRIPTION

Figure 1:
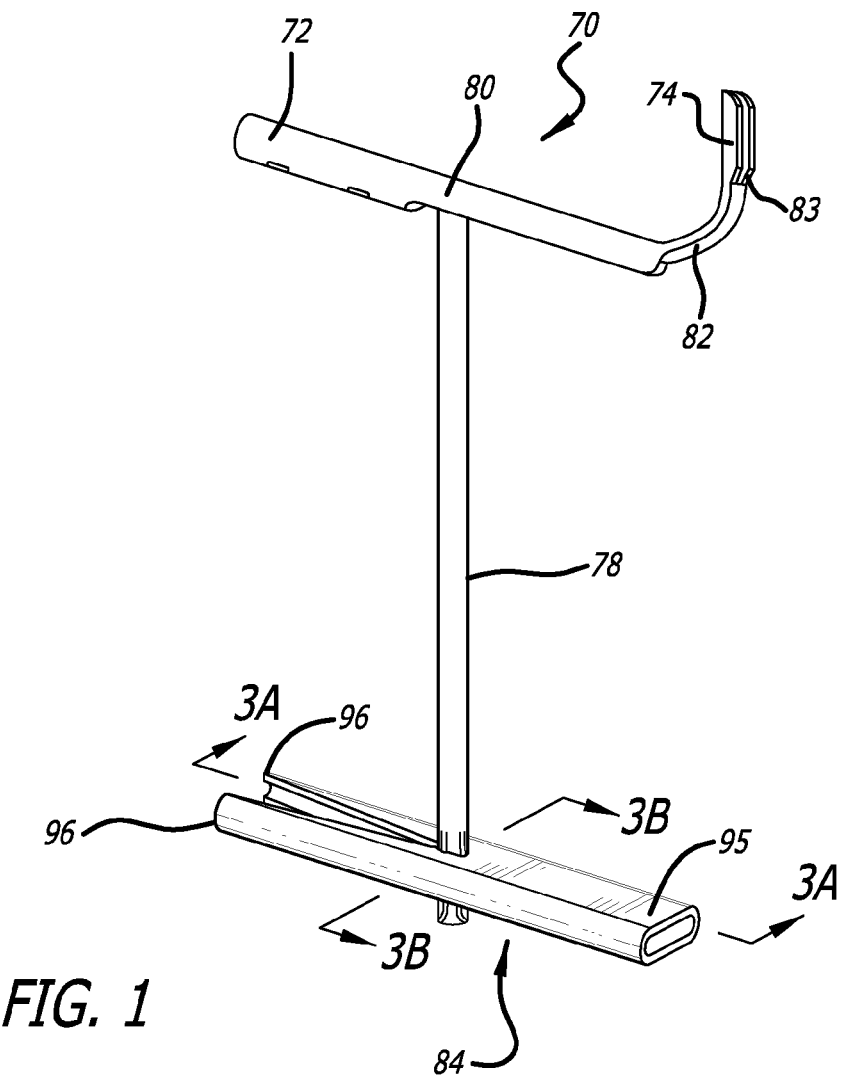
FIG. 1 is a perspective view of one embodiment of an anchor assembly that includes a distal anchor and a proximal anchor secured together by a suture.
Figure 2:
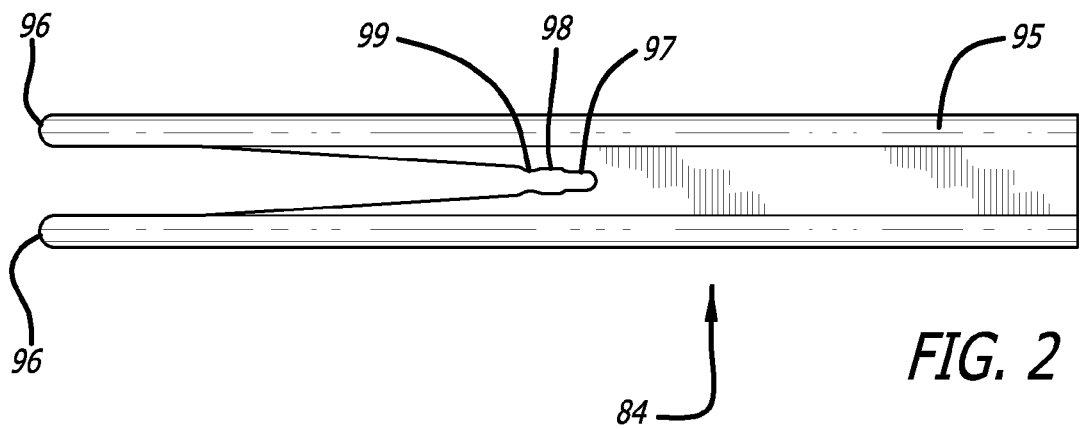
FIG. 2 is a top view of one embodiment of a slotted anchor.
Figure 3B:
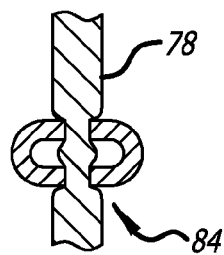
FIG. 3B is a cross section of the anchor assembly taken along lines 3B-3B of FIG. 1.
Figure 3A:
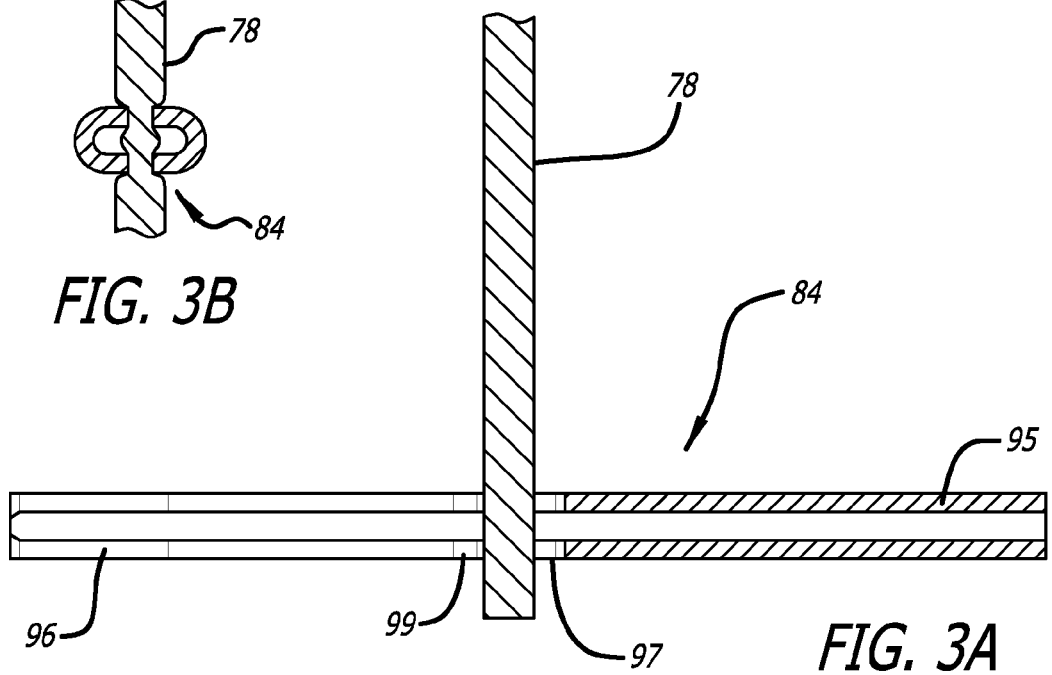
FIG. 3A is a cross section of the suture and the slotted anchor assembly taken along lines 3A-3A of FIG. 1.
Figure 4:
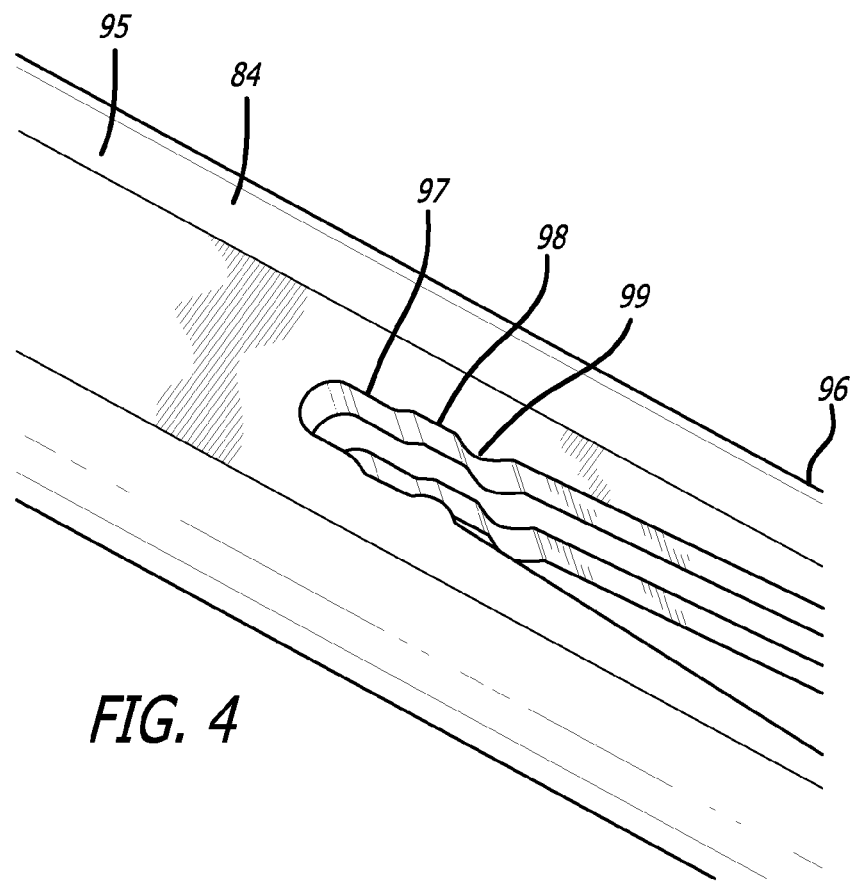
FIG. 4 is a close up perspective view of the slot inception, wider seating region, and inwardly facing protrusions of the slotted anchor of FIG. 2.

Turning now to the figures, which are provided by way of example and not limitation, the disclosed embodiments are illustrated with regard to anchor assemblies configured to be delivered within a patient's body. As stated, the disclosed embodiments can be employed for various medical purposes including but not limited to approximating, retracting, lifting, compressing, supporting or repositioning tissues, organs, anatomical structures, grafts or other material found within a patient's body. Such tissue manipulation is intended to facilitate the treatment of diseases or disorders. Moreover, the disclosed embodiments have applications in cosmetic or reconstruction purposes, or in areas relating to the development or research of medical treatments. Referring now to the drawings, wherein like reference numerals denote like or corresponding components throughout the drawings and, more particularly to FIGS. 1-7, there is shown an embodiment of an anchor assembly.

In such applications, one portion of an anchor assembly is positioned and implanted against a first section of anatomy. A second portion of the anchor assembly is then positioned and implanted adjacent to a second section of anatomy for the purpose of approximating, retracting, lifting, compressing, supporting or repositioning one section of anatomy with respect to the other section of anatomy, as well as for the purpose of approximating, retracting, lifting, compressing, supporting or repositioning one section of anatomy with respect to the other section of anatomy. It is also to be recognized that both a first and second portion of the anchor assembly can be configured to accomplish the desired approximating, retracting, lifting, compressing, supporting or repositioning of anatomy due to tension supplied thereto via a connector assembly (e.g., suture) affixed to the first and second portions of the anchor assembly.

In one embodiment of the anchor assembly, the anchor assembly is configured to include structure that is capable of being implanted within a patient's body. The anchor assembly may also be used in conjunction with a conventional remote viewing device (e.g., an endoscope) so that an interventional site can be observed.

In one embodiment, the anchor assembly can be placed at an intervention site using a delivery tool (See co-pending U.S. application Ser. No. 11/318,240). One specific, non-limiting application of the delivery tool is for the treatment of benign prostatic hyperplasia. In this procedure, an implant is delivered to a prostatic lobe that is obstructing the urethral opening and restricting flow. The implant compresses the lobe, thereby increasing the urethral opening and reducing the fluid obstruction through the prostatic urethra.

Additionally, in one embodiment, the anchor assembly is embodied in a tissue approximation anchor (TAA). The tissue approximation anchor is an implant assembly that includes one tubular member, referred to as the capsular anchor or, more generally, distal anchor 70. The distal anchor 70 is preferably connected by a suture (preferably polyester) 78 to a slotted, flattened-tubular member (preferably comprised of stainless steel), referred to as the urethral anchor or proximal anchor 84. In one specific, non-limiting embodiment, the distal anchor 70 is comprised of an electro-polished Nitinol (nickel titanium alloy SE508, 50.8% nickel) tube.

The tissue approximation anchor is designed to be useable in an office environment (in contrast to requiring a hospital environment) with a delivery tool. The delivery tool is used through a 19 Fr sheath in one preferred embodiment, while in another embodiment a sheath size of 21F is employed. Additionally, the material selection and construction of the tissue approximation anchor still allows for a subsequent TURP procedure to be performed, if necessary, on the prostate. In this suture-based, tissue approximation technique, a needle delivery mechanism (as described in U.S. application Ser. No. 11/318,246) is used to implant a nitinol distal anchor 70 and attached suture 78. Once the distal anchor 70 and attached suture 78 have been deployed, with the needle retracted and the suture 78 tensioned, the slotted anchor 84 is pushed by the delivery tool and captures the suture 78 transverse to the anchor axis. The flattened portion of the anchor 84 allows the anchor to be held by the tool without rotating so that it will stay oriented properly to ensure the suture enters the space between the prongs. In many of the illustrated embodiments, the seating region in the slotted anchor for the suture is shown in approximately the midpoint of the slotted anchor but it is within the scope of the present invention to locate the seating region closer to one end or the other of the anchor in order to prevent the ends of the prongs of the anchor from digging into tissue after implantation but rather sit more parallel to the tissue, if so desired.

In one embodiment, the nitinol tube is attached to a USP size 0 PET (Poly Ethylene Terephthalate) monofilament suture 78 by thermally forming the suture to locking features on the anchor 70. Referring again to the suture itself, the PET suture is a round monofilament extrusion/pulltrusion composed of a grade 8816 polyethylene terephthalate. Typically, the base material for the suture is annealed at approximately 100 degrees Celsius for approximately 130 minutes in a straight condition. In one non-limiting embodiment, the PET suture 78 has a diameter of 0.015 inches and a tensile strength greater than or equal to 12.7 pounds.

In one embodiment, the anchor 84 is a 316L stainless steel flattened tube that is slotted, electro-polished, and passivated. The anchor is depicted in the figures with a flat surface on the top or bottom but it is within the scope of the present invention that only one of the surfaces be flat and that the surface(s) do not have to be true flat but rather could have a slight dip or protrusion on the flattened surfaces. The slotted anchor 84 includes prongs 96 that grip and deform the suture 78 in the seating region 98 between the spaced prongs 96. It is to be recognized that rather than defining mirrored images, in one or more of the embodiments disclosed herein, the seating region can be formed by staggered structure or one prong can have a longer area defining seating structure than an opposing prong to provide an effective engagement for a particular suture or connector design. The prongs 96 are quite stiff and robust therefore subject to minimal to no deflection. In particular preferred embodiments, the prongs or overall width of the anchor adjacent the seating region 98 expands, after a connector has been seated in the seating region, less than about 0.002 inches (i.e., less than about five percent), more preferably less than about 0.001 inches (i.e., less than about two and half percent). In particular preferred embodiments, the prongs or overall width of the anchor adjacent the ends of the prongs 96 expands, after a connector has been seated in the seating region, less than about 0.0065 inches (i.e., less than about seventeen percent), more preferably less than about 0.006 inches (i.e., less than about fifteen percent). Due to its particular configuration, the slotted anchor 84 also requires less force to deploy onto a suture 78. Being relatively stiff, the prongs 96 of the slotted anchor 84 are significantly more resistant to bending. The four individual edges/faces (two on each prong 96) of the slotted anchor 84 disrupt the surface of the suture 78, both biting into the suture 78 as well as compressing the suture 78 between the slotted prongs 96, including sometimes melting the suture locally due to the pressure and heat created during deployment of the slotted anchor onto the suture. The reduced area of contact provided by this structure as well as multiple planes of engagement of the anchor slot to the connector strengthens connections and prevents inadvertent separation. Additionally, the narrow width of the slot inception 97 is substantially smaller than the connector diameter, with the purpose to allow the stiffer prongs to slightly elastically expand over the connector and contribute to anchor retention by means of compression but not intended to receive the connector into this relief slot, which is positioned proximal to the seating portion 98. It is beneficial in some circumstances however for the slotted anchor to be pushed far enough on to the connector such that the connector becomes at least partially seated in the slot inception relief slot so that it becomes pinched and/or wedged. In this circumstance, a two-part compression slot is created wherein the short, narrow part of the slot ensures a good mechanical interlock but my compromise the strength of the suture locally and the second wider part is ensures a good mechanical interlock but without any compromise in the strength of the suture. Notably, the outwardly stepped slot width also has a dimension smaller than the connector diameter, and receives the connector with some interference.

In one embodiment, the prongs 96 are formed from a wide (or flattened) tubular structure. The wider and smoother prongs 96 of the anchor 84 assist in preventing the prongs 96 from irritating and/or damaging tissue, which is more likely to occur with a thinner and pointier leg structure forming piercing structure. Further, in one embodiment, the slot in the anchor 84 is configured to create registering and aligning surfaces to the delivery tool (not shown). In several embodiments, the two inner surfaces of the prongs 96 of the slotted anchor 84 are configured as corresponding inwardly facing U-shapes. In this configuration, the inner surfaces of the prongs 96 bite into the suture 78. In still other embodiments, the two inner surfaces of the prongs 96 of the slotted anchor 84 are configured to present a notched geometry. In still other embodiments, the inner surfaces of the prongs are configured with burrs, roughened edges, serrations, etc. to enhance their ability to retain the connector.

In several embodiments, such as for example FIGS. 1-7, the slotted anchor 84 includes a rigid generally tubular or flattened cylindrical back end 95, extending from which are a pair of spaced prongs 96. Optionally, the anchor assembly may be filled in with a radiopaque material, or other therapeutic agent. Terminal ends of the prongs 96 may be tapered to receive a section of the suture 78. Notably, the prong structure commences at a narrowed slot inception 97, which steps outwardly to a wider dimension to thereby define the space between the prongs 96. This narrow slot 97 provides the slotted anchor 84 with desired structural rigidity to receive the suture 78 and to facilitate locking engagement with the slotted anchor 84. Notably, the space between the prongs 96 of the slotted anchor 84 is dimensioned relative to the diameter of the suture 78 such that is has sufficient gripping force moving toward the seating region 98 to obviate the need for a securing end unit. Accordingly, in a preferred embodiment, a securing end unit is not needed. Moreover, it is to be recognized that the slot inception 97 is not intended to receive a connector or suture 78 but rather it provides the prongs with the slight flexibility to receive the suture 78 in a manner so that the suture 78 is positioned as desired within the seating region. Such desired positioning creates a lock between the anchor 84 and the suture 78 thereby providing the clinical benefit of preventing loss of tension between members forming an anchor assembly.

As described above, in one embodiment, shaped tube raw stock is used to produce the anchor 70 and the anchor 84 using slot/profile cutting. Specifically, in one embodiment the raw stock may be cut by laser, wire-EDM, or stamped from a flat and formed into a shape. In one non-limiting embodiment, the raw stock has a total height ranging from 0.020 inches to 0.025 inches, and has a total width ranging from 0.038 inches to 0.040 inches. Thus, this raw stock is flatter and wider than a purely round tube would be.

The inwardly facing protrusion region 99 on the prongs 96 is configured to keep the suture 78 from "walking" out over time. In one embodiment, the inner surface of the prongs 96 near the slot inception 97 is more of an extended landing (i.e., wider seating region 98) than a simple U-shaped surface configuration. Various of the contemplated embodiments can include such landings and the landings can assume curved or other shapes. Additionally, the inner surface of the prongs 96 can have alternative configurations differing from a U-shape. Non-flat inner surfaces tend to facilitate retention of a suture 78 under tension such as exemplified in FIG. 3B which depicts a suture forming a hourglass shape between opposing surfaces of prongs 96. The outer surfaces of the prongs 96 are contemplated to define an atraumatic structure such as that provided by curved surfaces. In one embodiment, there is a longer root diameter for better seating of the suture 78. In such an embodiment, the prongs 96 have a straight lead-in initially before beginning to taper. In another embodiment (See FIGS. 5 and 6), the prongs have a tapered lead-in configuration with additional inward protrusions 100. This tapered lead-in configuration with additional inward protrusions 100 assists with the centering of the suture 78 into the seating region 98 and facilitated placement of the anchor onto the suture 78.

In one embodiment, a 0.014 inch gap between prongs 96 provides a structure suitable for use with a 0.015 inch suture 78 while allowing minimal to no tissue impingement. In another approach, the seating region 98 of the slot has a 0.008 inch gap while the inwardly protruding region 99, which helps prevent a suture 78 from walking out over time, has a 0.006 inch gap. In still another embodiment, the seating region 98 of the slot has a 0.009 inch gap, while the inwardly protruding region 99, has a 0.007 inch gap. In one embodiment, seating region 98 is approximately 0.011 inches.

These configurations create a lower resistance interference fit to achieve reliable seating while maintaining strength. It will be appreciated by those skilled in the art, that many variations in the slot parameters are possible for optimizing performance in different situations. Additionally, in some embodiments, the protrusions formed on opposite prongs may be of differing shapes. Such slot parameters include, by way of example only, and not by way of limitation: width, thickness, length, and profile.

Figure 8:
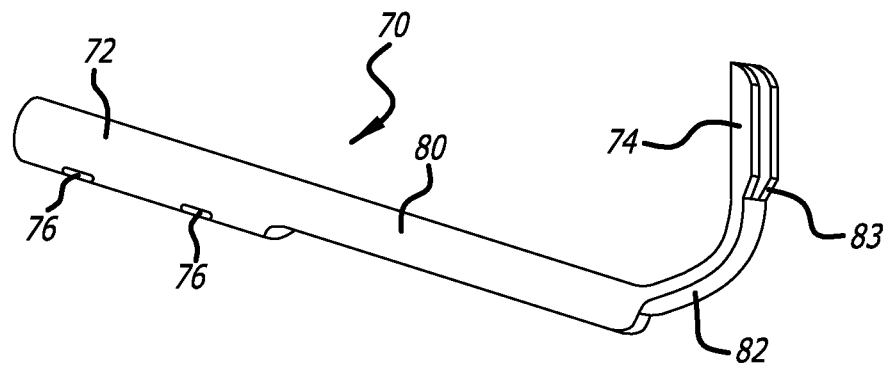
FIG. 8 is a perspective view of the distal anchor with a orthogonally oriented tail portion.
Figure 9:
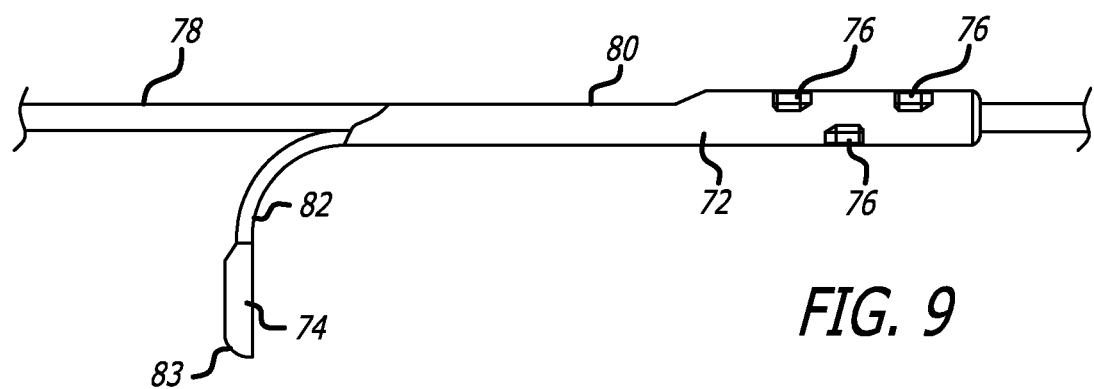
FIG. 9 is a side view of the distal anchor with a orthogonally oriented tail portion of FIG. 8 and the suture in an in-line configuration.
Figure 10:
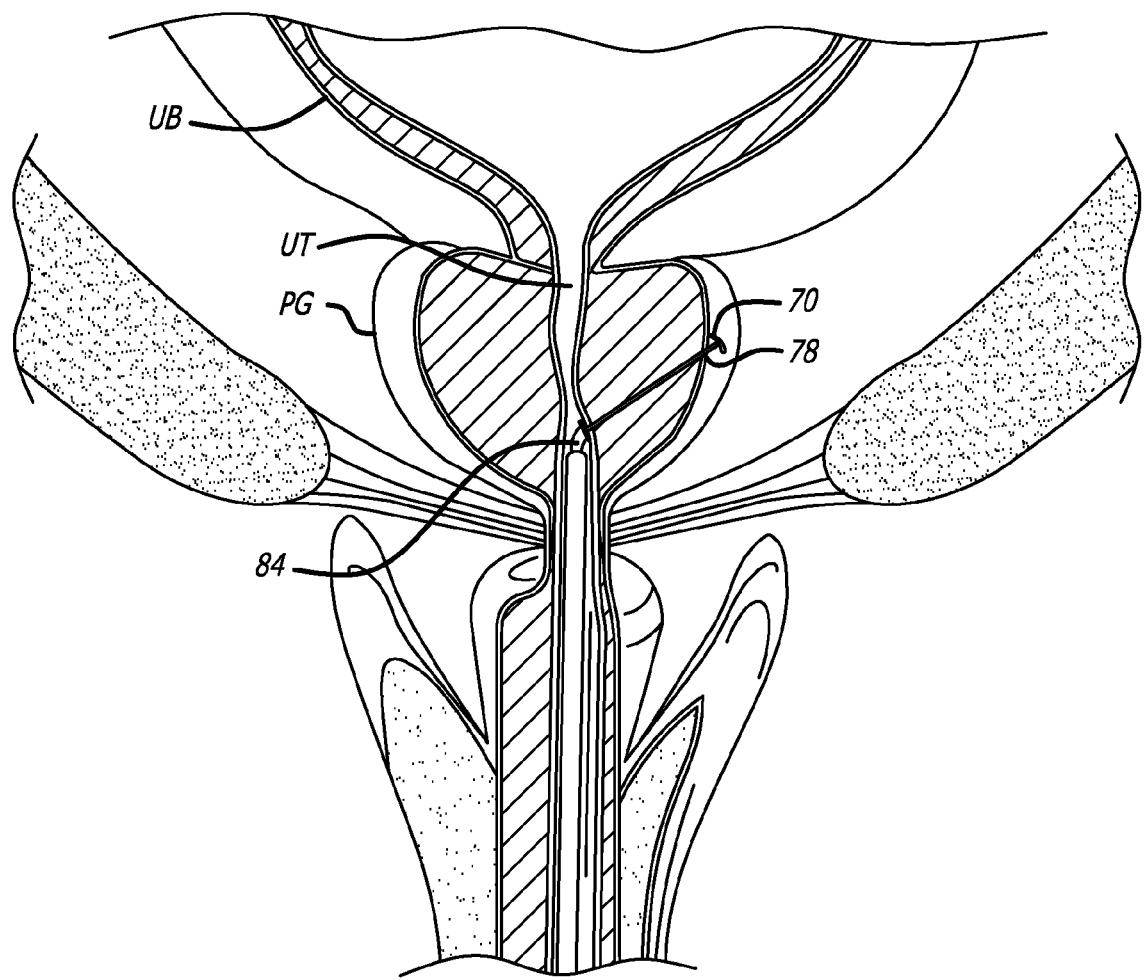
FIG. 10 is a cross sectional view of an anchor assembly of FIG. 1 implanted through the prostate of an individual with benign prostatic hyperplasia.

One embodiment of an anchor assembly 10 is depicted in FIGS. 8-10. In its unconstrained configuration, the anchor 70 includes a tubular (head) portion 72 which is generally orthogonally oriented to a tail portion 74. It is to be noted, however, that while housed in a delivery assembly and prior to deployment at a target area, the anchor 70 is constrained to define a generally straight configuration, only subsequently assuming the unconstrained (i.e., orthogonally oriented) configuration upon deployment from a delivery device.

The anchor 70 is laser cut or wire EDM (electrical discharge machined) from a Nitinol base stock that is generally-tubular in shape. The nitinol anchor is shape-set to have a "flipping tail" and is electro-polished. The suture 78 is then attached to the anchor 70. Specifically, in one embodiment, the PET suture 78 is thermoformed onto locking features in the anchor 70. The anchor 70 may be locally heated to re-flow the suture onto the end of the anchor 70 and into cutouts on the anchor 70. Continuing, in one non-limiting embodiment, the post electro-polished anchor 70 has a 0.016 inner diameter and a 0.0245 outer diameter.

In one non-limiting embodiment, the tubular portion 72 of the anchor 70 includes a plurality of tabs 76 which can be deformed or deflected to accomplish affixing the anchor 70 to a suture 78. It has been found that three such tabs 76, two on one side of the tubular portion 72 and one on an opposite side, provide a sufficient connecting force. However, the anchor 70 may be attached to the suture 78 through any of several known techniques, such as by being attached to the distal end of the tubular portion 72.

In another aspect of a non-limiting embodiment, it is contemplated that the anchor 70 can be laser cut from a tube formed of Nitinol or other appropriate material. A mid-section 80 of the distal anchor 70 provides a structural transition from the tubular portion 72 to the tail portion 74. As such, a portion of a side wall is removed in the mid-section area 80. A further portion of the side wall is removed to define a connector section 82 of the tail 74 which extends from the mid-section 80. In one embodiment, this connector section 82 includes a bend that creates the orthogonally or obliquely oriented configuration. This connector section 82 acts as a barb or deflected strut to cause rotation of the anchor 70 relative to the suture 78 after deployment from a delivery tool (creating a "flipping tail") and produce the relative unconstrained (orthogonally oriented) angle assumed between the tail 74 and tubular portion 72 of the anchor 70. The recovered shape of the terminal end portion 83 of the anchor presents a transverse strut that engages tissue when the suture is tensioned.

Thus, in its implanted form (FIG. 1), the anchor assembly can include an anchor 70 (e.g., first anchor) whose initial engagement with a suture 78 is generally coaxial, and an anchor 84 (e.g., second anchor) with an initial engagement being generally perpendicular with the suture 78. The anchor 70 is "unsheathed" from a needle delivery device (not shown) once positioned for reliable deployment An anchor assembly ejected from a terminal end of a delivery device and implanted across a prostate is shown in FIG. 10.

A number of additional embodiments of the slotted anchor are described. It is to be recognized that the previous and below disclosed structures can be used for many applications. However, each of these disclosed embodiments may include structure accomplishing an engagement with a connector without requiring a secondary locking component. Such a secure engagement can be provided by an interference between anchor structure and the connector resulting in deformation of the connector.

Referring now to FIGS. 11-12, an embodiment of a slotted anchor 1184 having a flattened tubular shape is shown. In this embodiment, the slotted anchor 1184 has a width in lateral cross-section that is greater than its thickness, as well as tapered prongs 1196 that meet at a circular slot inception 1197 after passing inwardly facing protrusions 1199 and a seating region 1198 for the suture 78. This embodiment lacks a "relief slot" at the slot inception 1197 (as shown in FIGS. 5-7), but instead has only the above-described circular seating region 1198 for receiving the suture 78.

Figure 13:
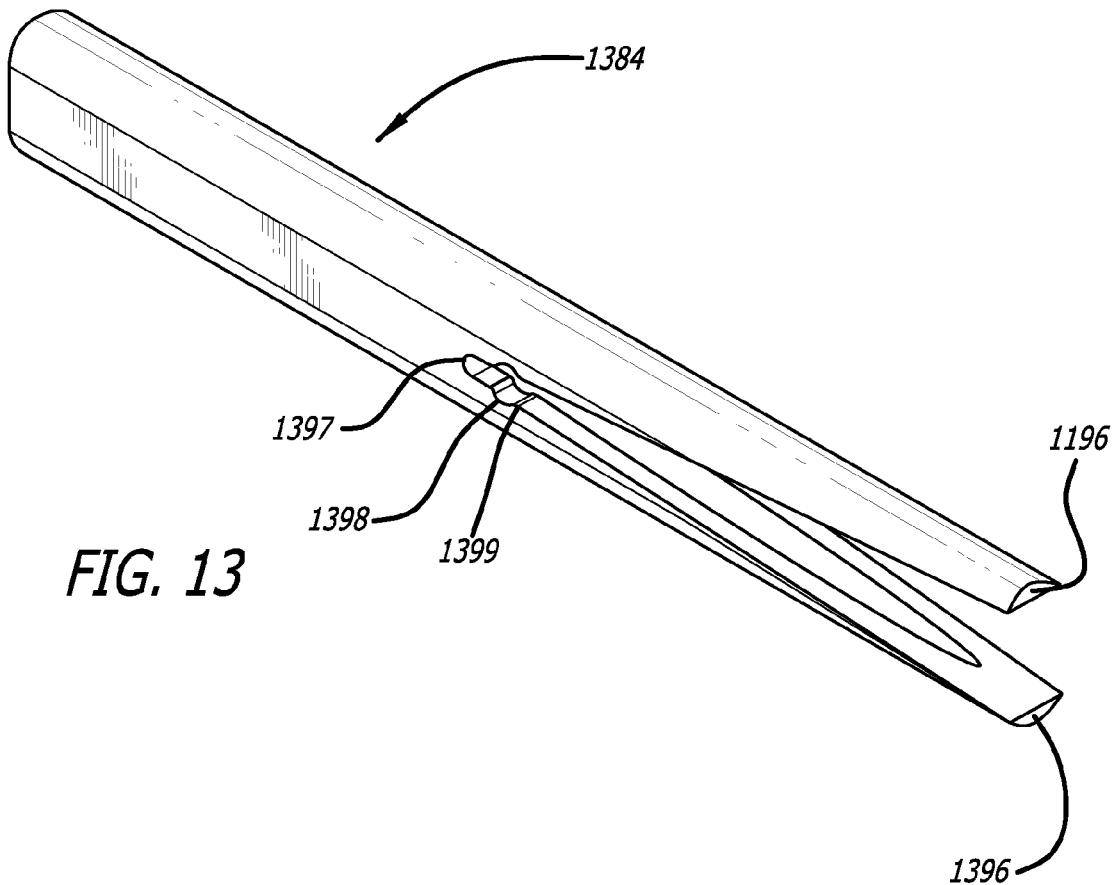
FIG. 13 is a perspective view of a slotted anchor having tapered prongs that converge towards a circular seating region before the slot inception.
Figure 14:
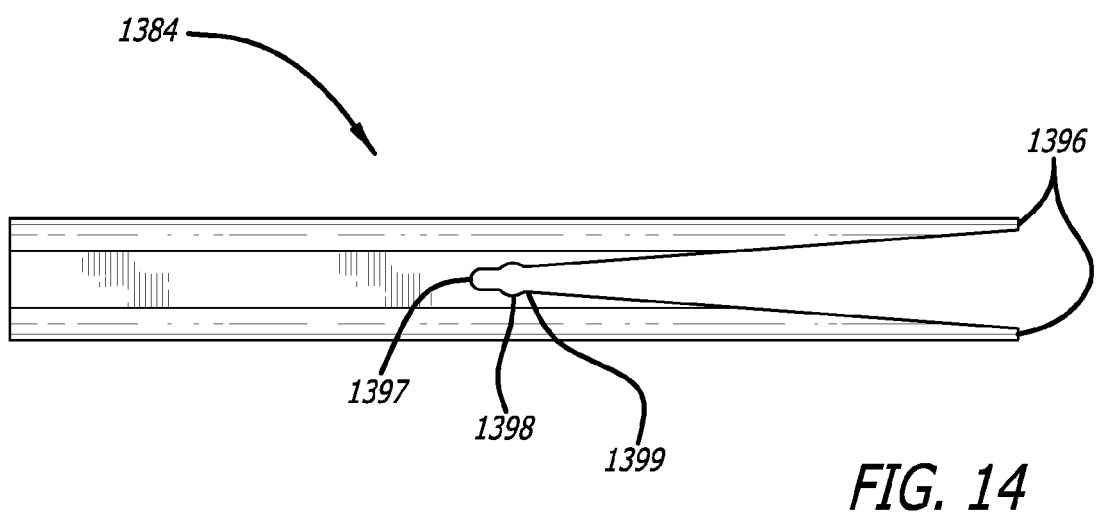
FIG. 14 is a top view of the slotted anchor of FIG. 13.

FIGS. 13-14 illustrate an embodiment of a slotted anchor 1384 having a flattened tubular shape. In this embodiment, the slotted proximal anchor 1384 has a width in lateral cross-section that is greater than its thickness. The anchor further includes tapered prongs 1396 that converge towards a circular seating region 1398 after passing inwardly facing protrusions 1399 and before reaching a generally U-shaped, more narrowly dimensioned slot inception 1397. This embodiment includes a "relief slot" at the slot inception 1397 for receiving the suture 78. Additionally, the relief slot may reduce stress concentration in the anchor when the suture is seated.

Figure 15:
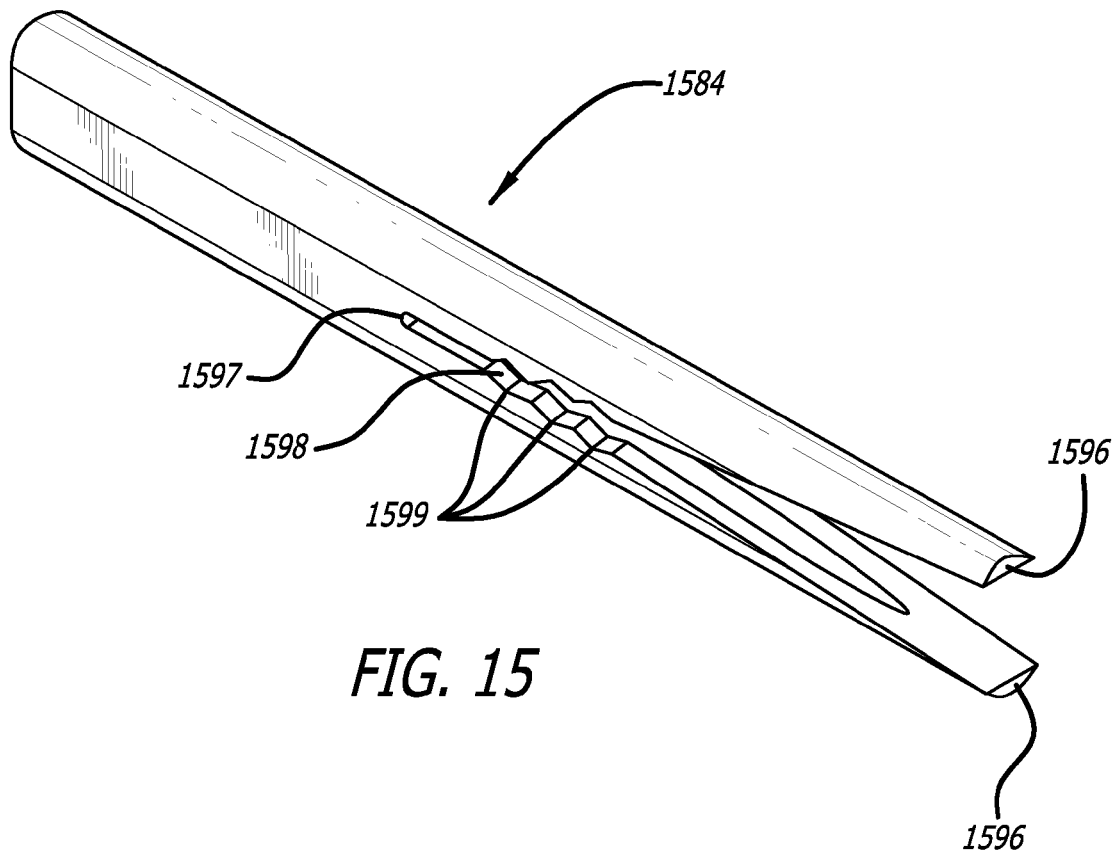
FIG. 15 is a perspective view of a slotted anchor having tapered prongs that converge towards a serrated seating region before the slot inception.
Figure 16:
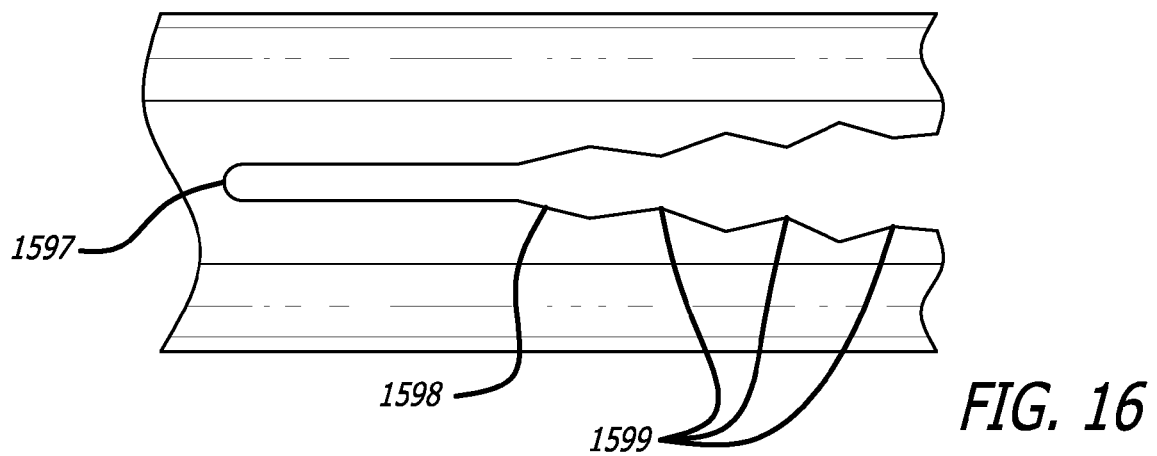
FIG. 16 is a close up top view of the slotted anchor of FIG. 15.

Referring now to FIGS. 15-16, an embodiment of a slotted anchor 1584 also having a flattened tubular shape is shown. In this embodiment, the slotted anchor 1584 includes tapered prongs 1596 that converge towards a seating region 1598 after passing a plurality of inwardly facing serrated protrusions 1599 and before the slot inception 1597. Here, as the serrated region 1599 tapers towards the seating region 1598, the surfaces forming apices of the serrated region have generally equal dimensions. It is also to be recognized that the serrated region 1599 can also define or embody a portion of a seating region. The serrated region 1599 can function to lock into and grasp a connector to thereby result in a firm engagement as well as provide a lower surface area for contacting a suture being placed therethrough. The apices of the serrated region cause more deformation than many of the previously discussed surfaces without abrading the suture 78.

Figure 17:
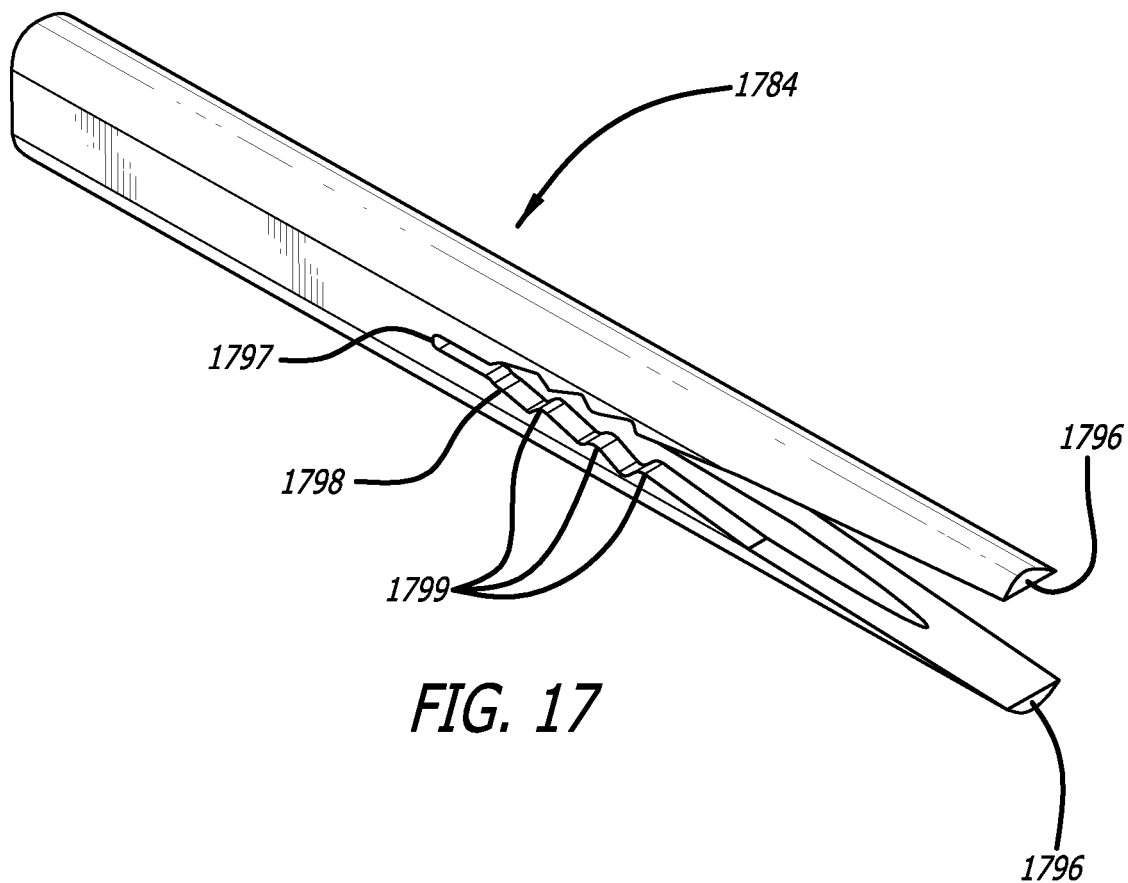
FIG. 17 is a perspective view of a slotted anchor having tapered prongs that converge towards a barbed seating region before the slot inception.
Figure 18:
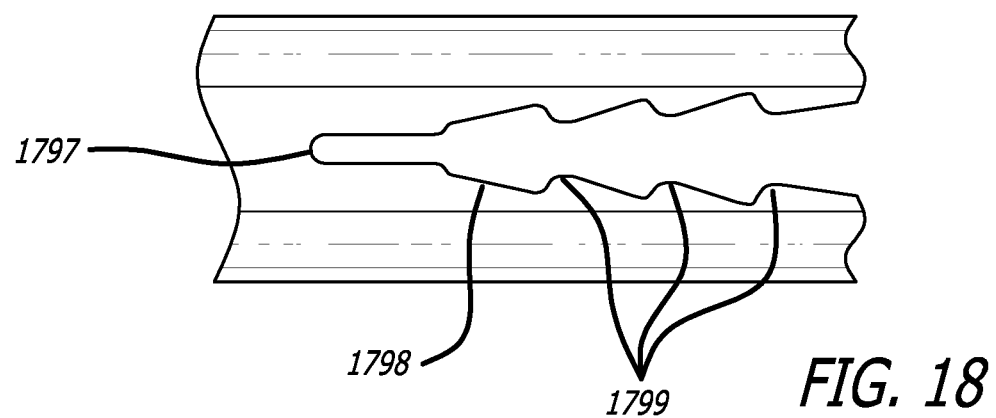
FIG. 18 is a close up top view of the slotted anchor of FIG. 17.

Another embodiment of a slotted anchor 1784 having a flattened tubular shape and a serrated region is shown in FIGS. 17-18. In this embodiment, tapered prongs 1796 converge towards a seating region 1798 extending from a slot inception 1797 after passing a serrated region formed by inwardly facing barbed protrusions 1799. The barbed protrusions 1799 of the serrated region are formed by surfaces of different dimensions, thus forming more of a barbed shape. Such a barbed shape is intended to facilitate sufficient gripping forces on a suture 78. A slotted proximal anchor 1784 with a barbed serrated region preferably is used in conjunction with a tougher type of suture 78 that is resistant to abrasion.

Figure 19:
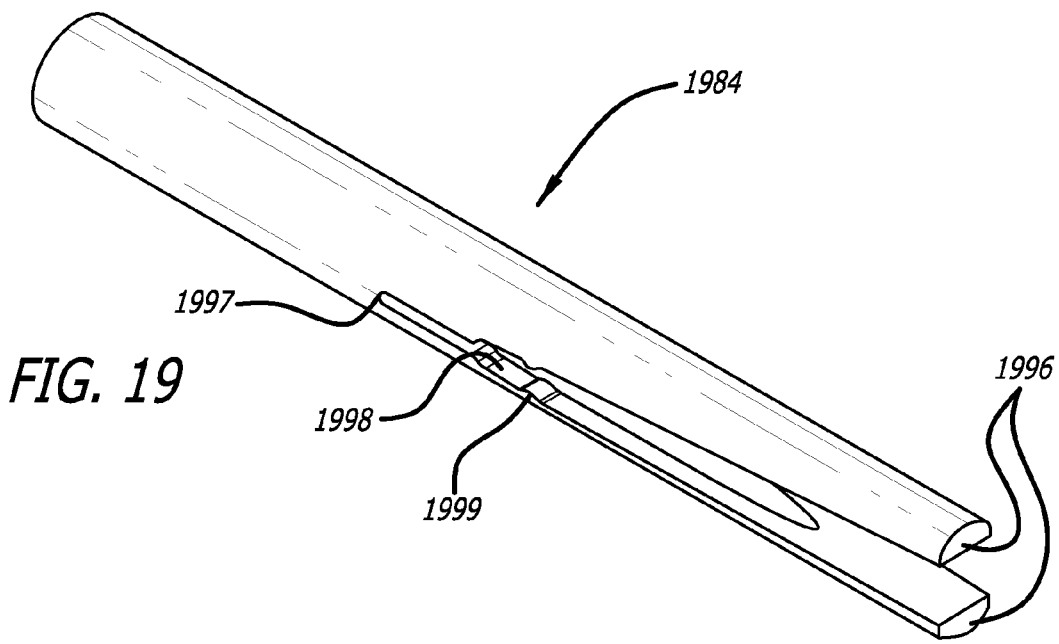
FIG. 19 is a perspective view of a slotted anchor having a tubular shape and tapered prongs that converge towards inwardly facing protrusions in the seating region before the slot inception.
Figure 20:
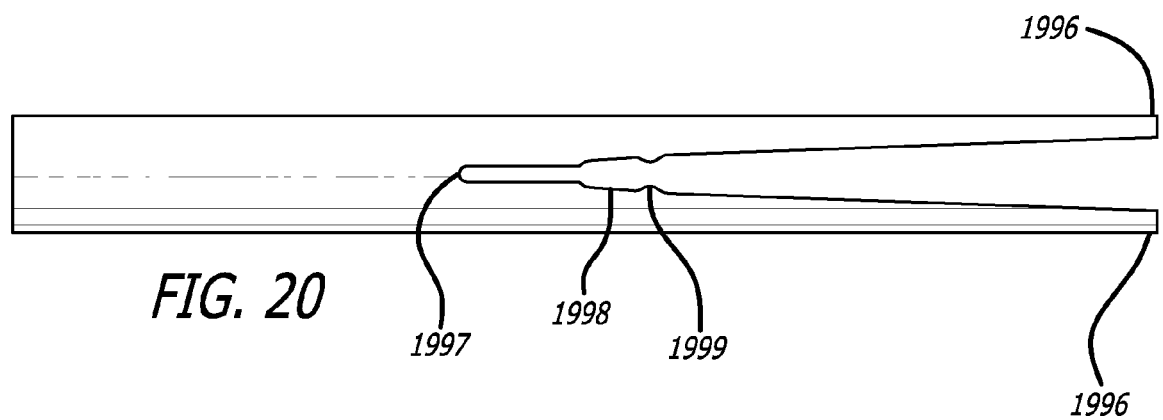
FIG. 20 is a side view of the slotted anchor of FIG. 19.
Figure 21:
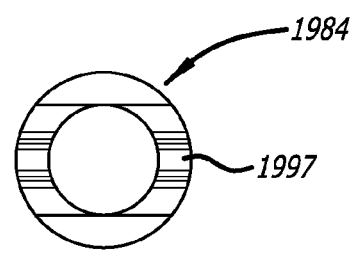
FIG. 21 is an end view of the slotted anchor of FIG. 19.

Referring now to FIGS. 19-21, yet a further embodiment of a slotted anchor 1984 having a tubular shape is shown. In this embodiment, the slotted proximal anchor 1984 has tapered prongs 1996 that converge toward inwardly facing protrusions 1999 adjacent the seating region 1998 before reaching the slot inception 1997. In combination, the angle formed by the tapered prongs, the protrusion and relatively narrow dimension of the seating region cooperate to create a substantial engagement with a connector. Preferably, the protrusions 1999 cause moderate deformation of the suture 78 while minimizing abrasion of the suture.

Figure 22:
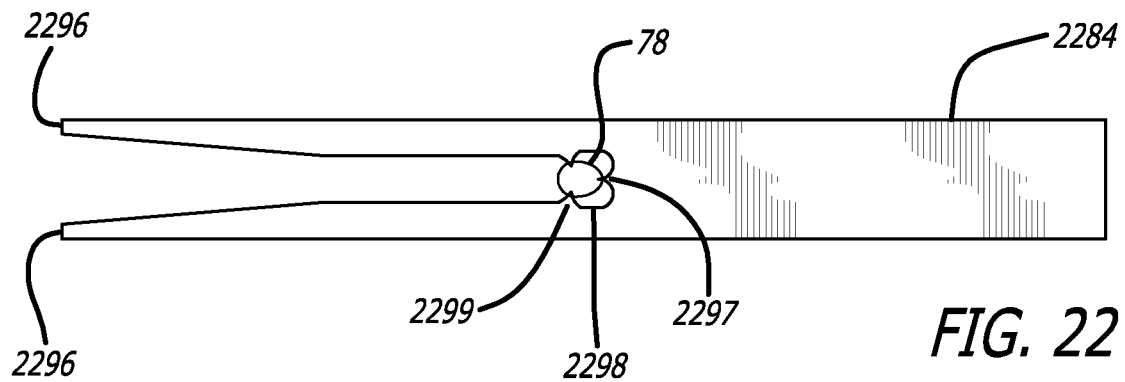
FIG. 22 is a top view of a slotted anchor having prongs that begin a tapered convergence before turning parallel towards a triple-barbed slot inception.
Figure 23:
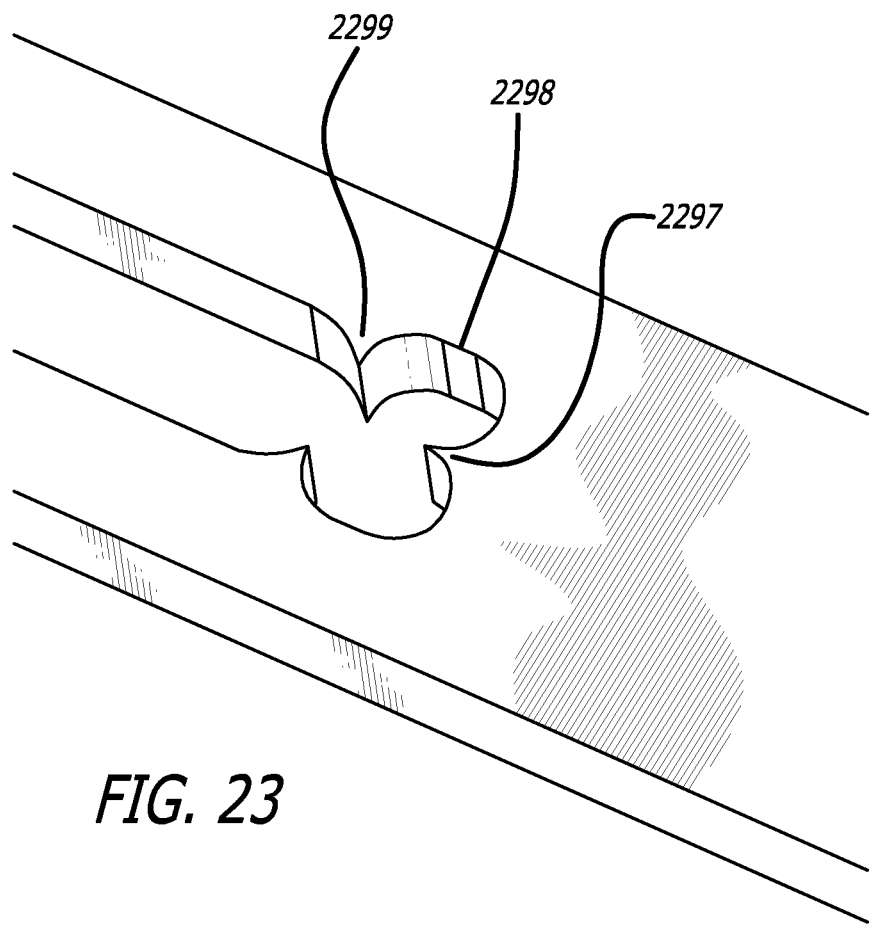
FIG. 23 is a close up perspective view of the top layer of the slotted anchor of FIG. 22.

FIGS. 22-23 show an embodiment of a slotted anchor 2284 having a generally rectangular shape and that has been formed by stamping a flat sheet of metal that is folded over at the leading end of the prongs 2296 to form two layers (only one layer is shown). In this embodiment, the slotted anchor 2284 has a width in lateral cross-section that is greater than its thickness. The anchor also includes prongs 2296 that define a tapered convergence before turning parallel towards inwardly facing barbed protrusions 2299, one projecting from each prong. The anchor also includes a seating region 2298 configured adjacent a barbed slot inception 2297. The barbed slot inception 2297 and barbed protrusions 2299 cooperate to deform and grasp a suture 78. Preferably, these barbed protrusions create more point pressure or "bite" into the suture 78 and therefore is contemplated to be used in conjunction with a tougher type of suture 78 that is more resistant to abrasion.

Figure 24:
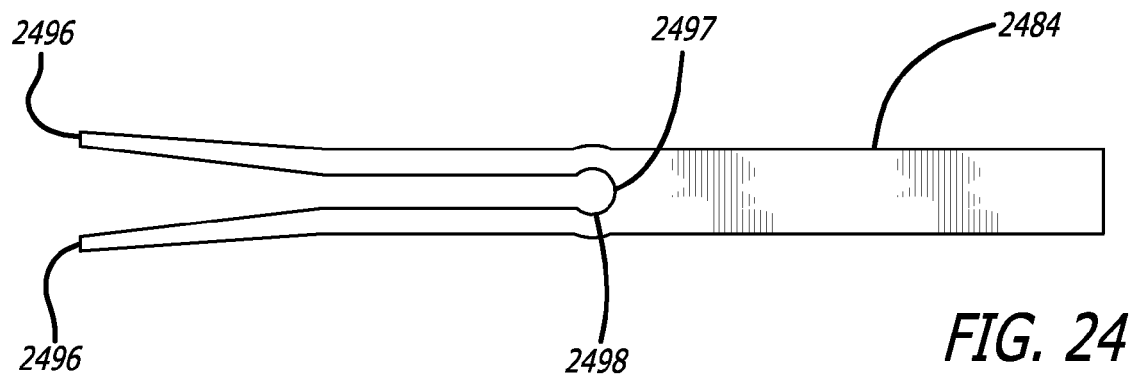
FIG. 24 is a top view of a slotted anchor having prongs that begin a tapered convergence before turning parallel towards a circular slot inception.
Figure 25:
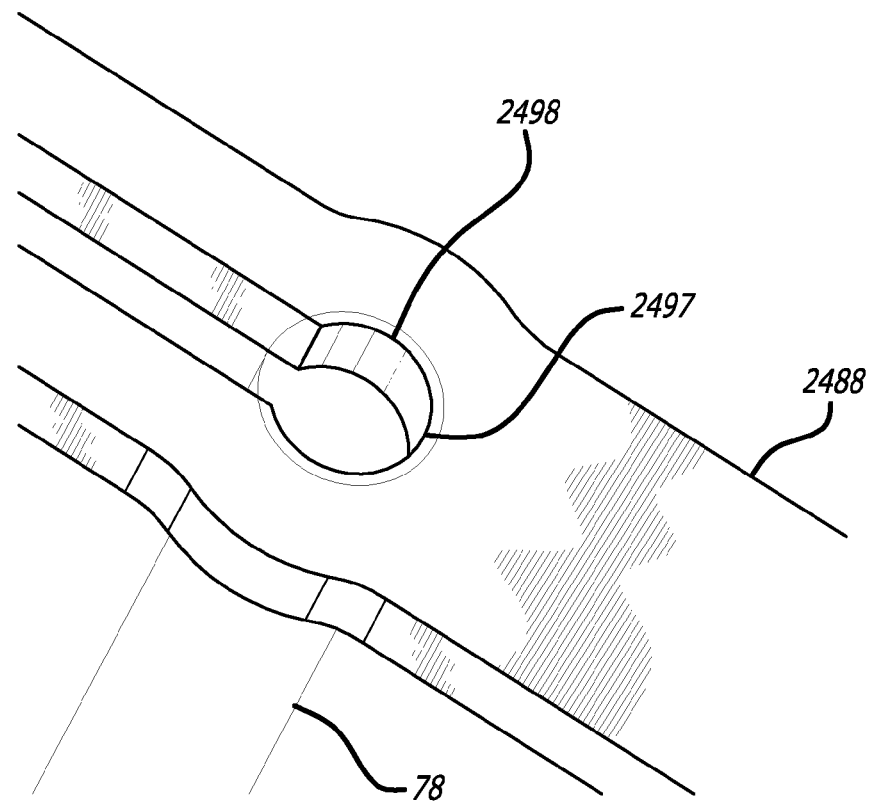
FIG. 25 is a close up perspective view of the top layer of the slotted anchor of FIG. 24.

Referring now to FIGS. 24-25, there is shown another embodiment of a slotted anchor 2484 having a generally rectangular portion that has been formed by folding over a flat sheet (only one layer is shown). In this approach, the slotted proximal anchor 2484 has a width in lateral cross-section that is greater than its thickness transverse to the axis of the suture 78, and prongs 2496 that begin a tapered convergence before turning parallel towards a seating region 2498 formed at a circular slot inception 2497. This circular slot inception 2497 creates a compression ring to secure the suture 78. This type of compression ring tends to deform the suture 78 without abrading the suture 78 (i.e., less "bite" into the suture). This embodiment also has expanded width prongs 2496. In this manner, the terminal ends of the prongs 2496 diverge in a manner such that they span a dimension greater than the width of the rectangular portion. Such structure facilitates receiving the connector and guides it to the seating region 2498 as the anchor 2484 is moved into engagement with the suture.

Figure 26:
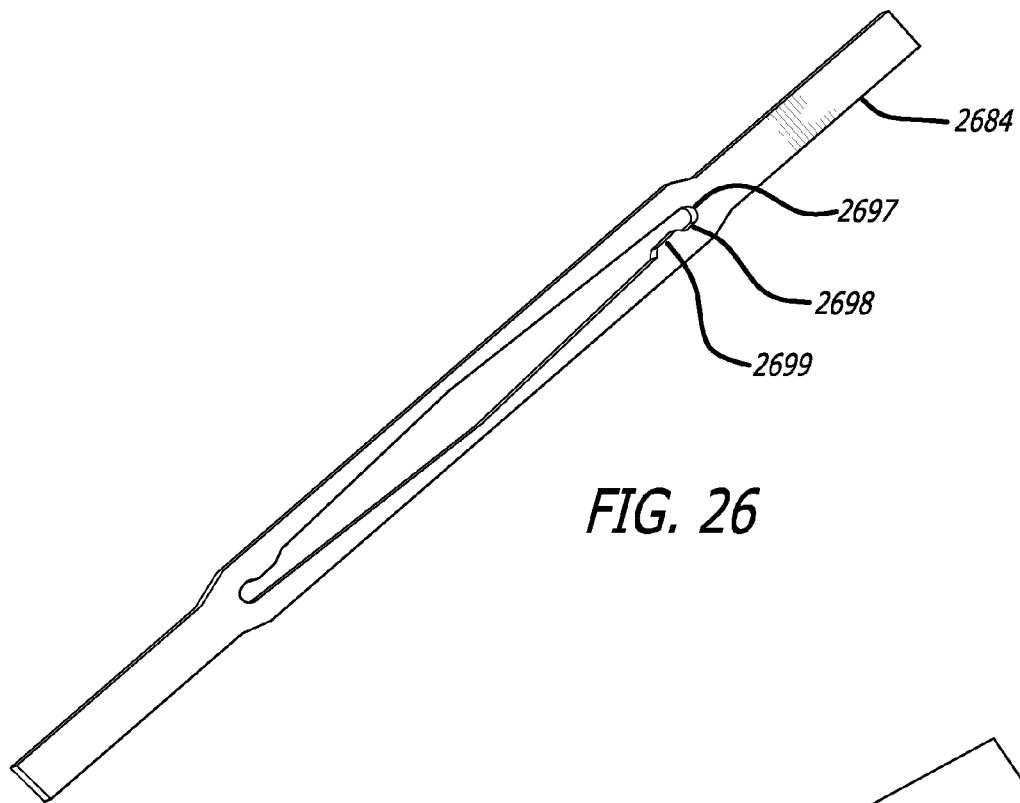
FIG. 26 is a perspective view of an unfolded slotted anchor, wherein one side of the anchor has an inwardly protruding seating region that is an inverted configuration from the other side of the inwardly protruding seating region of the anchor.
Figure 27:
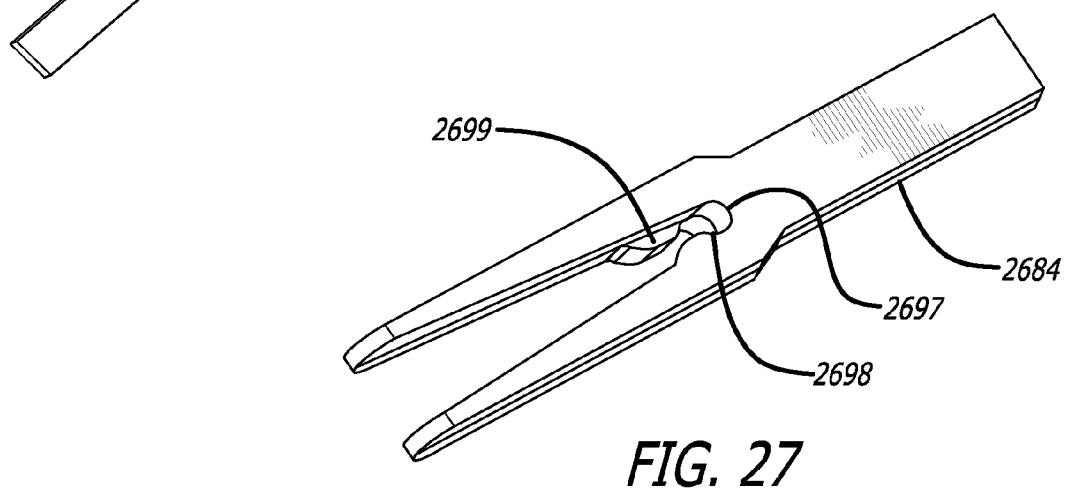
FIG. 27 is a perspective view of the folded slotted anchor of FIG. 26.
Figure 28:
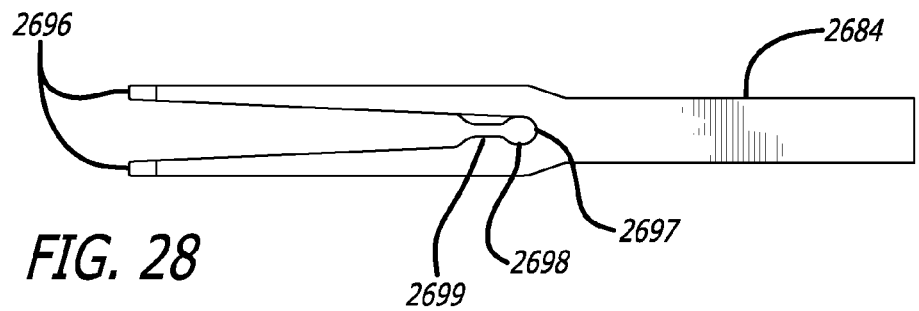
FIG. 28 is a top view of the folded slotted anchor of FIG. 26.

As shown in FIGS. 26-28, and as best seen in FIG. 27, another embodiment of a slotted anchor 2684 has tapered prongs 2696 that converge toward inward protrusions 2699 and a seating region 2698 before reaching the circular slot inception 2697. This anchor 2684 can be formed by stamping or cutting of flat metal stock to produce an elongated member and then folding the member in half. When folded, the pattern formed into the structure defines the inward protrusions 2699, seating region 2698, and circular slot inception 2697. Otherwise stated, in this embodiment, one side of the anchor 2684 has inward protrusions 2699 that are an inverted configuration from the inward protrusions 2699 on the other side of the anchor 2684 to form structure well suited to grip a connector. This embodiment has an oblong seating region 2698 for receiving the suture 78. After the elongated member is folded, a unitary body may be produced by tack welding or laser welding the anchor 2684 together. This type of slotted anchor 2684 is generally easier to manufacture.

Figure 29:
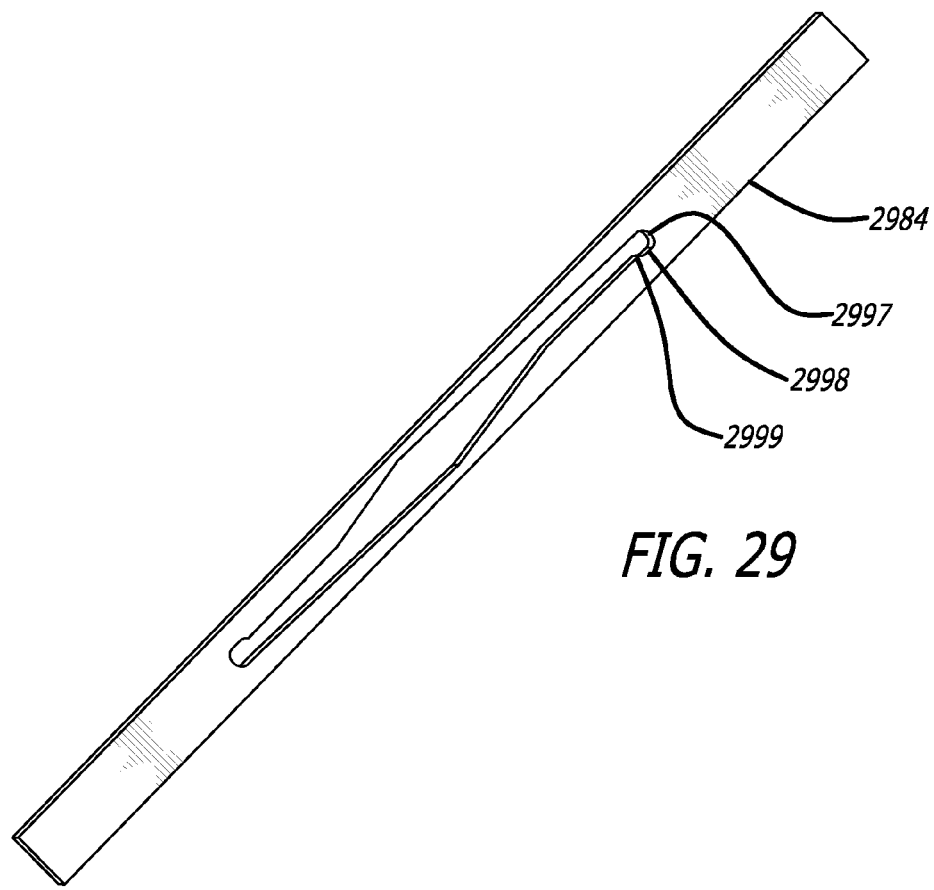
FIG. 29 is a perspective view of an unfolded slotted anchor having oppositely tapered prongs that converge towards the oblong slot inception.
Figure 30:
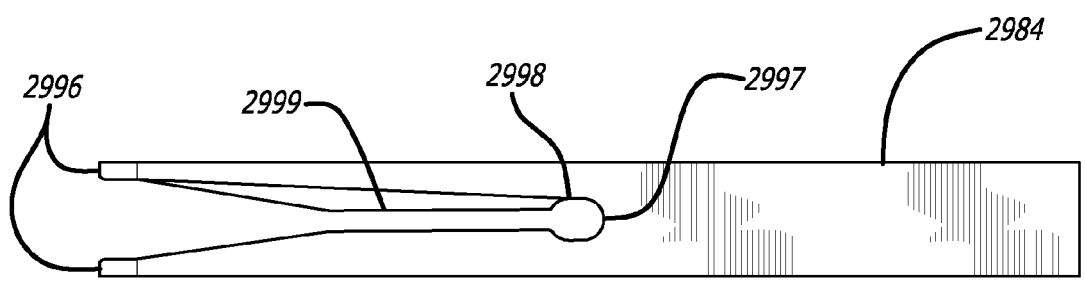
FIG. 30 is a top view of the folded slotted anchor of FIG. 29.

Referring now to FIGS. 29-30, another embodiment of a slotted anchor 2984 formed from a folded member is shown. In this approach, when folded, the slotted proximal anchor 2984 has a width in lateral cross-section that is greater than its thickness and oppositely tapered prongs 2996 that converge toward inward protrusions 2999 and a seating region 2998 before reaching the slot inception 2997. Additionally, in this embodiment one side of the anchor 2984 has oppositely tapered prongs 2996 that are an inverted configuration from the other side of the oppositely tapered prongs 2996 of the anchor 2984. This embodiment has an oblong seating region 2998 for receiving the suture 78.

Figure 31:
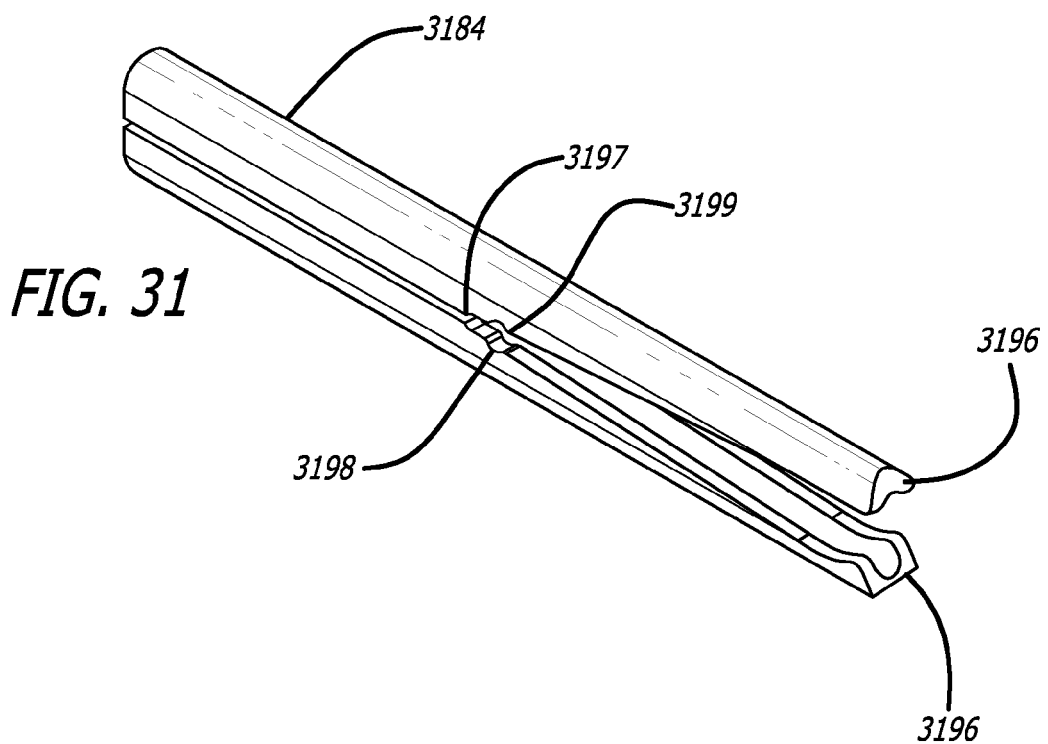
FIG. 31 is a perspective view of a slotted anchor having a slit in its top along its length.
Figure 32:
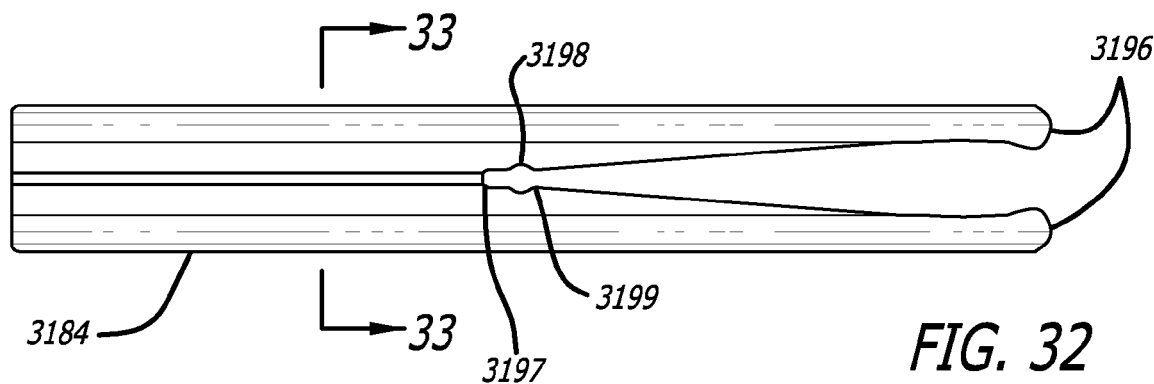
FIG. 32 is a top view of the slotted anchor of FIG. 31.
Figure 33:
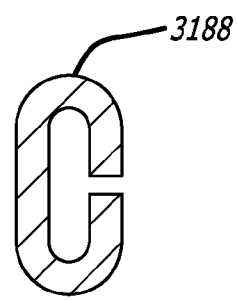
FIG. 33 is a cross-sectional view of the slotted anchor of FIG. 31 taken along line 33-33 of FIG. 32.

FIGS. 31-33 depict an embodiment of a slotted anchor 3184 having a slit that extends along its top. This anchor is produced using an alternative forming technique, namely the flat sheet is rolled along its length rather than being folded at its ends as described before. Thus, in cross-section the anchor defines a C-shape (See FIG. 33). In this embodiment, the slotted anchor 3184 again has a width in lateral cross-section that is greater than its thickness and includes tapered prongs 3196. The prongs 3196 converge toward inward protrusions 3199 and continue to a circular seating region 3198 before reaching the slot inception 3197. Additionally, in this embodiment the prongs 3196 include inwardly facing protrusions at their terminal ends that increase the stiffness of the prongs 3196, as well as reducing possible irritation of the surrounding tissue when implanted. If desired, during manufacturing, the anchor 3184 can be clamped down to close the slit that extends along its length. As described above, a unitary body may be produced by tack welding or laser welding the anchor 2984 together in some embodiments.

Figure 34:
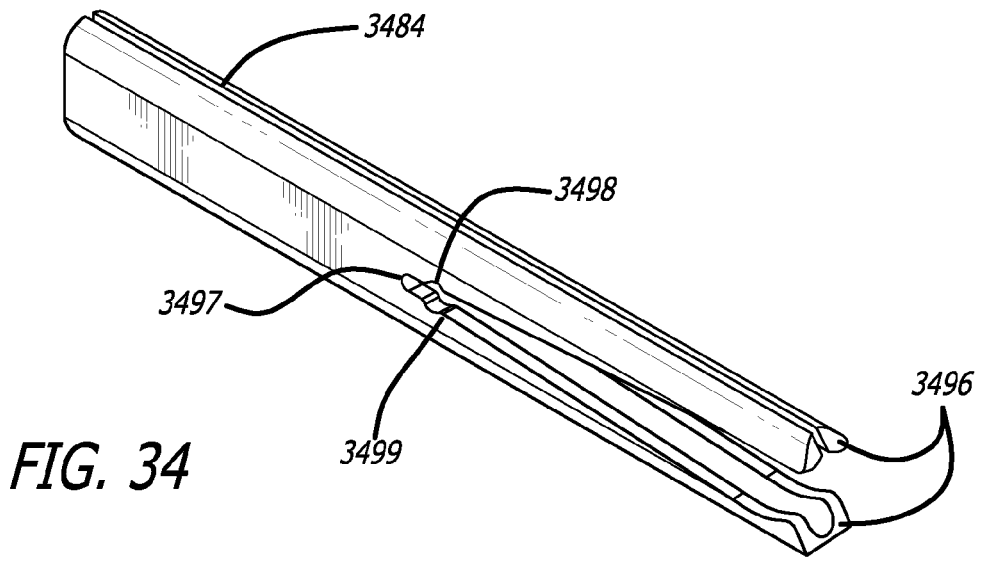
FIG. 34 is a perspective view of a slotted anchor having a slit in its side along its length.
Figure 35:
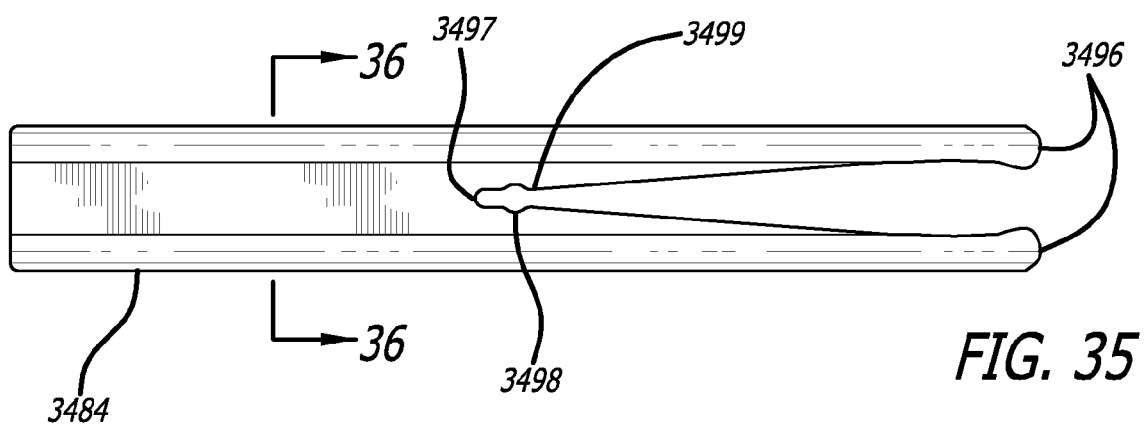
FIG. 35 is a top view of the slotted anchor of FIG. 34.
Figure 36:
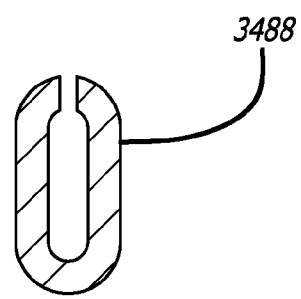
FIG. 36 is a cross-sectional view of the slotted anchor of FIG. 34 taken along line 36-36 of FIG. 35.

Referring now to FIGS. 34-36, an embodiment of a slotted anchor 3484 having a slit extending along the outside wall of one of the prongs 3496. Here, a cross-section of the anchor 3484 defines a U shape (See FIG. 36). In this embodiment, the slotted anchor 3484 has a width in lateral cross-section that is greater than its thickness and tapered prongs 3496 that converge toward inward protrusions 3499 and a circular seating region 3498. The circular seating region 3498 is configured adjacent a slot inception 3497. Additionally, the prongs 3496 include inwardly facing protrusions at their terminal ends.

Figure 37:
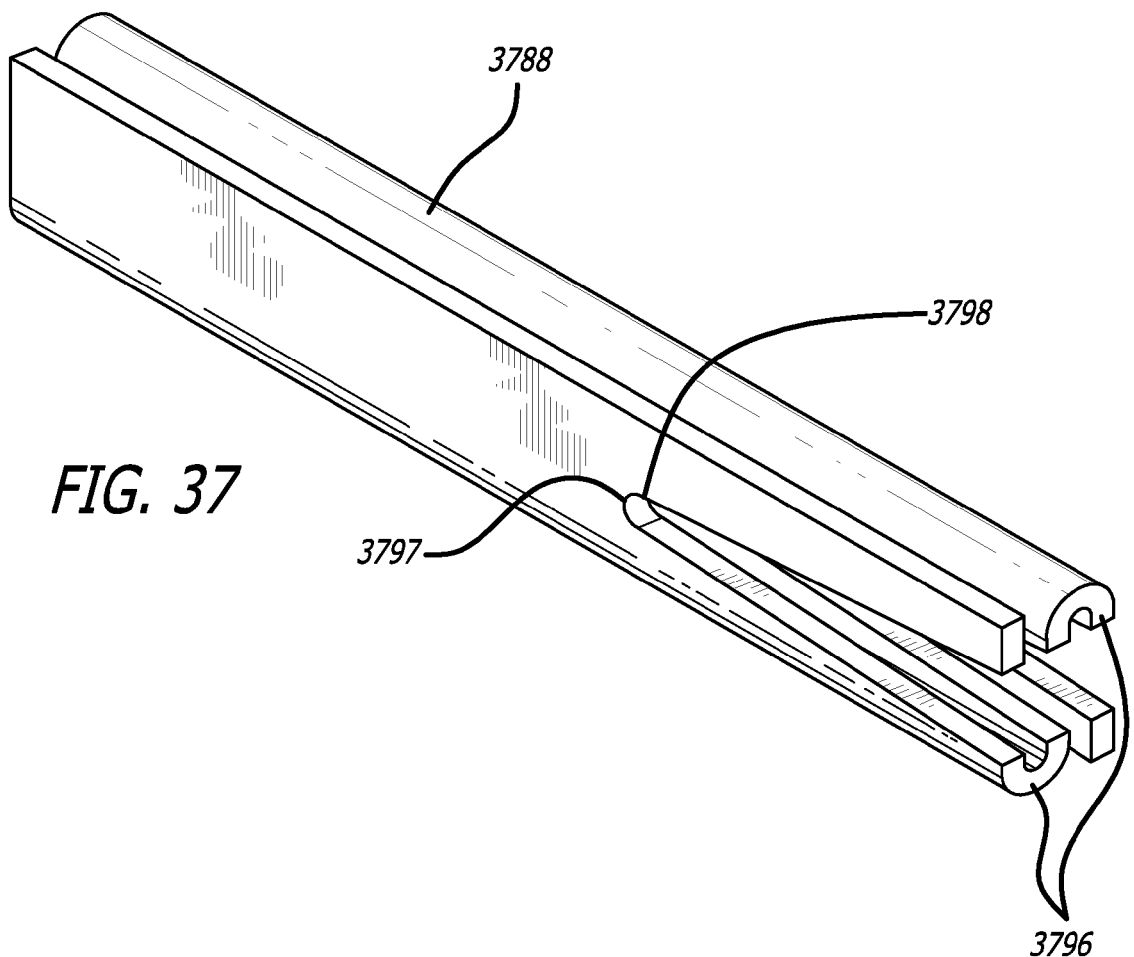
FIG. 37 is a perspective view of a slotted anchor wherein the top half of the anchor has an inverted configuration from the bottom of the anchor to create three slots of intersection with the suture.
Figure 38:
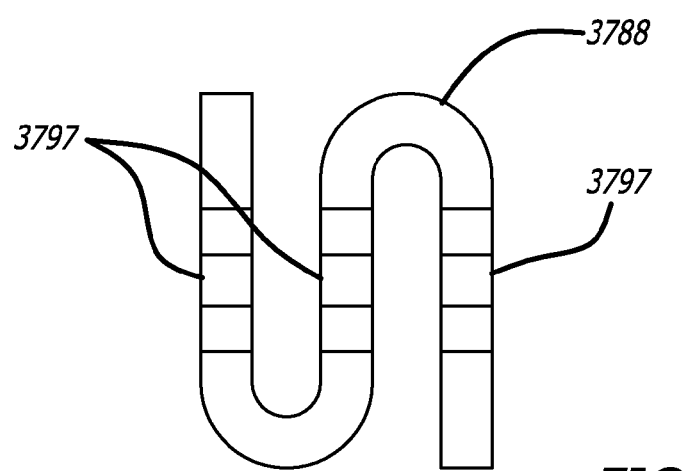
FIG. 38 is an end view of the slotted anchor of FIG. 37.

In still another embodiment, a slotted anchor 3784 that is formed from an S-shaped folded member is depicted in FIGS. 37-38. In this embodiment, the slotted anchor 3784 includes structure forming tapered prongs 3796 that converge towards a semi-circular seating region 3798 formed adjacent the slot inception 3797. Additionally, in this embodiment the top half of anchor 3784 has an inverted configuration from the bottom of the anchor 3784 to create multiple places capable of intersecting with a suture. In this embodiment, the prongs 3196 generate three layers for gripping the suture. It is within the scope of the present invention to provide multiple layers of engagement with the suture.

Figure 39:
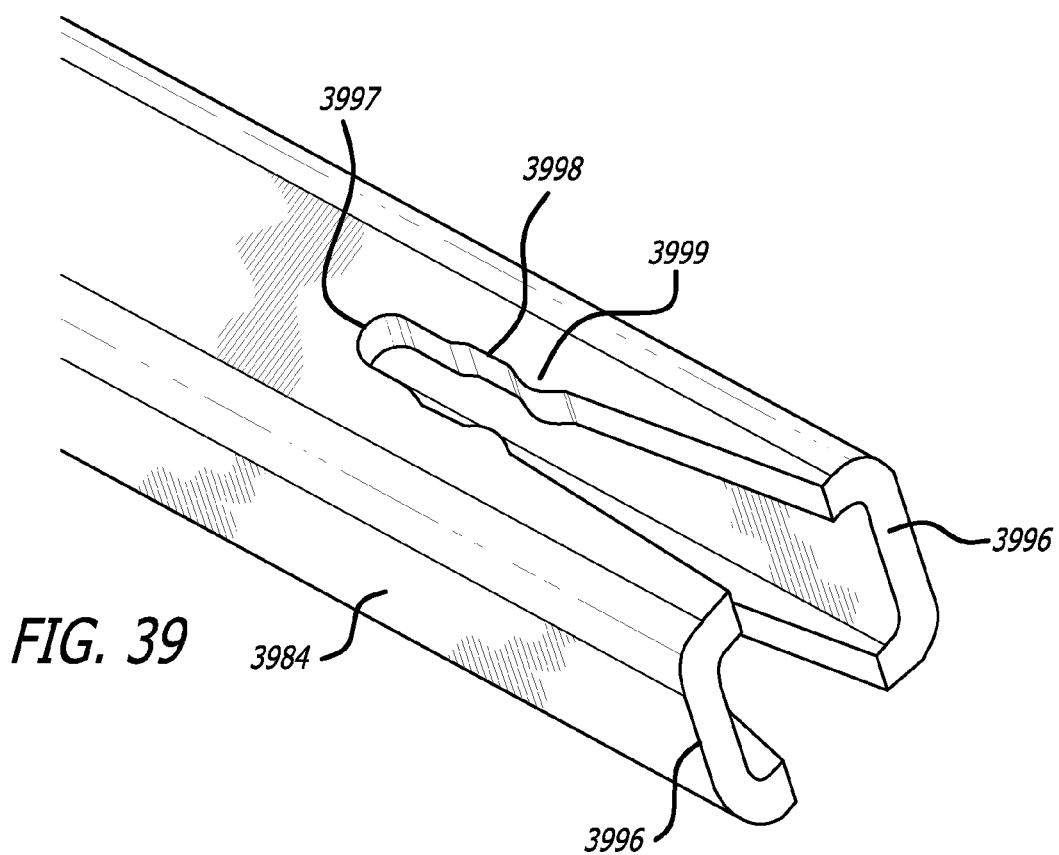
FIG. 39 is a perspective view of a slotted anchor that is substantially square in cross-section, but is otherwise similar to the slotted anchor of FIG. 4.

Referring now to FIG. 39, an embodiment of a slotted anchor 3984 is shown. The slotted anchor 3984 is quite similar to the slotted anchor 84 shown in FIG. 4, except that the slotted anchor 3984 of FIG. 39 is substantially square in cross-section. Additionally, the prongs 3996 of the slotted anchor 3984 are significantly shorter than the prongs 96 of the slotted anchor 84 shown in FIG. 4. This embodiment includes a "relief slot" at the slot inception 3997 and a seating region 3998.

Figure 40:
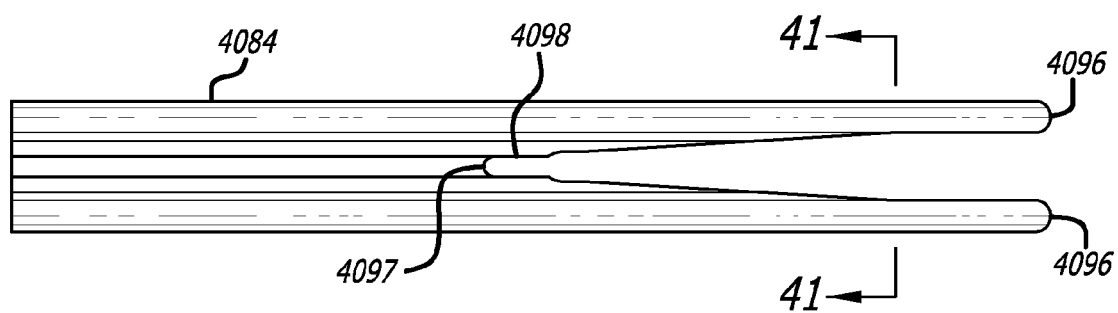
FIG. 40 is a top view of a slotted anchor that incorporates a slit along its top, and is formed into a substantially square shaped member in cross-section that is folded over on itself towards its center
Figure 41:
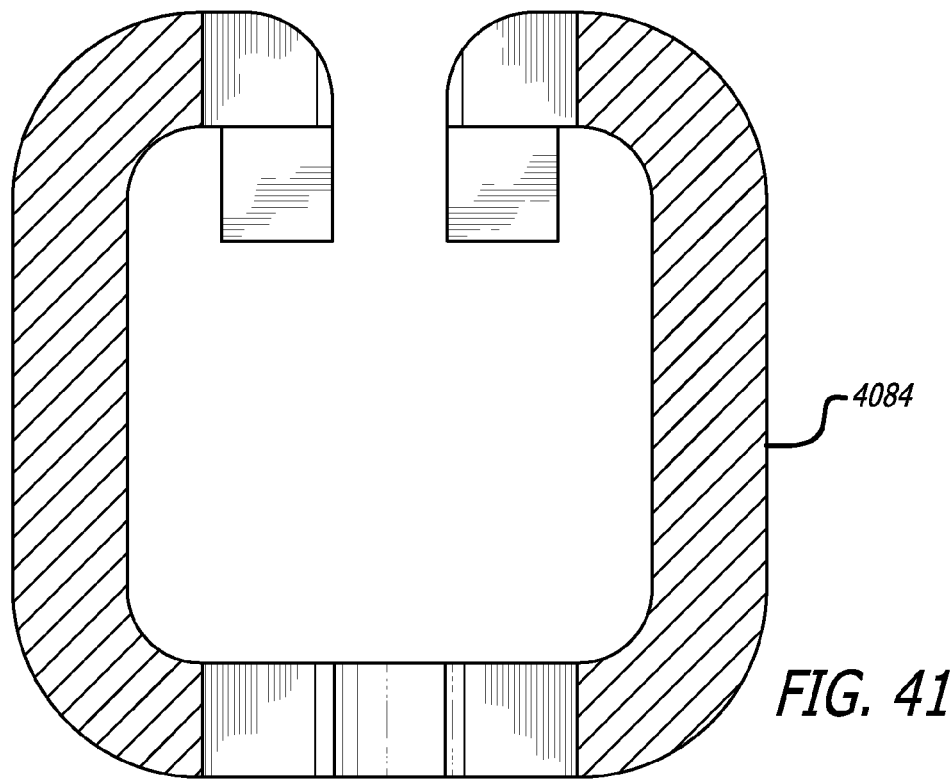
FIG. 41 is a cross-sectional view of the slotted anchor of FIG. 40.
Figure 42:
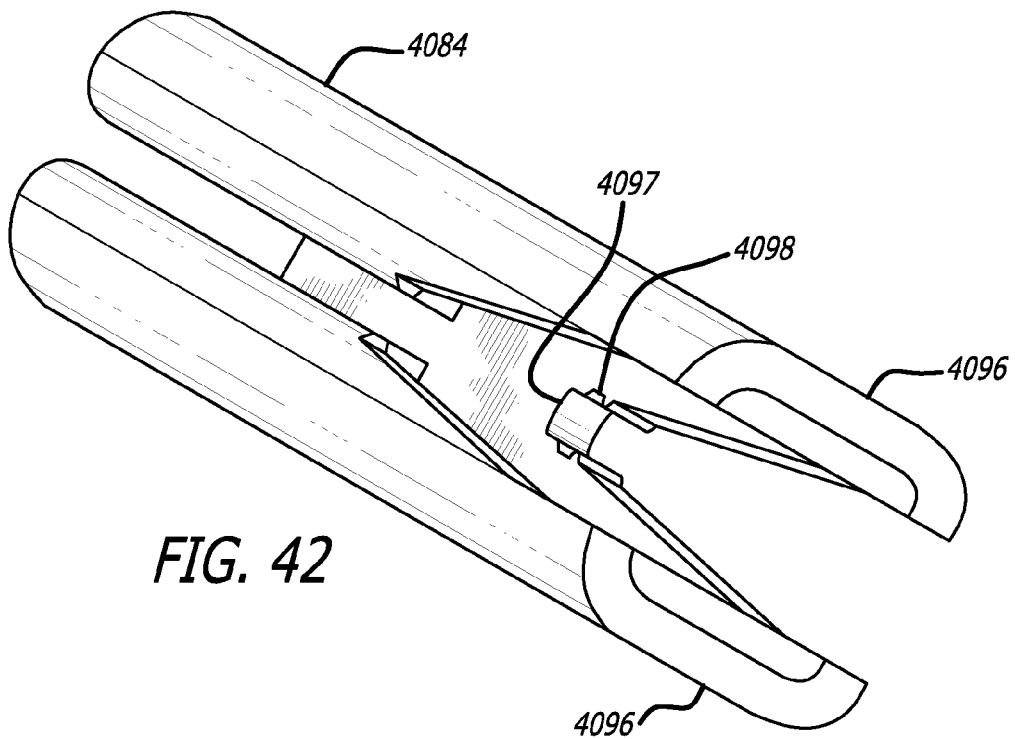
FIG. 42 is a perspective view of the slotted anchor of FIG. 40.

In another embodiment depicted in FIGS. 40-42, a slotted anchor 4084 incorporates a slit in its top, and is formed into a substantially square shaped member that is folded over on itself towards its center. This "folded over" region produces a greater surface area that is in contact with the suture 78, and thus, creates a larger amount of deformation of the suture 78 and friction against the suture 78. In this embodiment, the slotted anchor 4084 includes a structure forming tapered prongs 4096 that converge towards protrusions 4099 and a seating region 4098 formed adjacent to the slot inception 4097.

Figure 43:
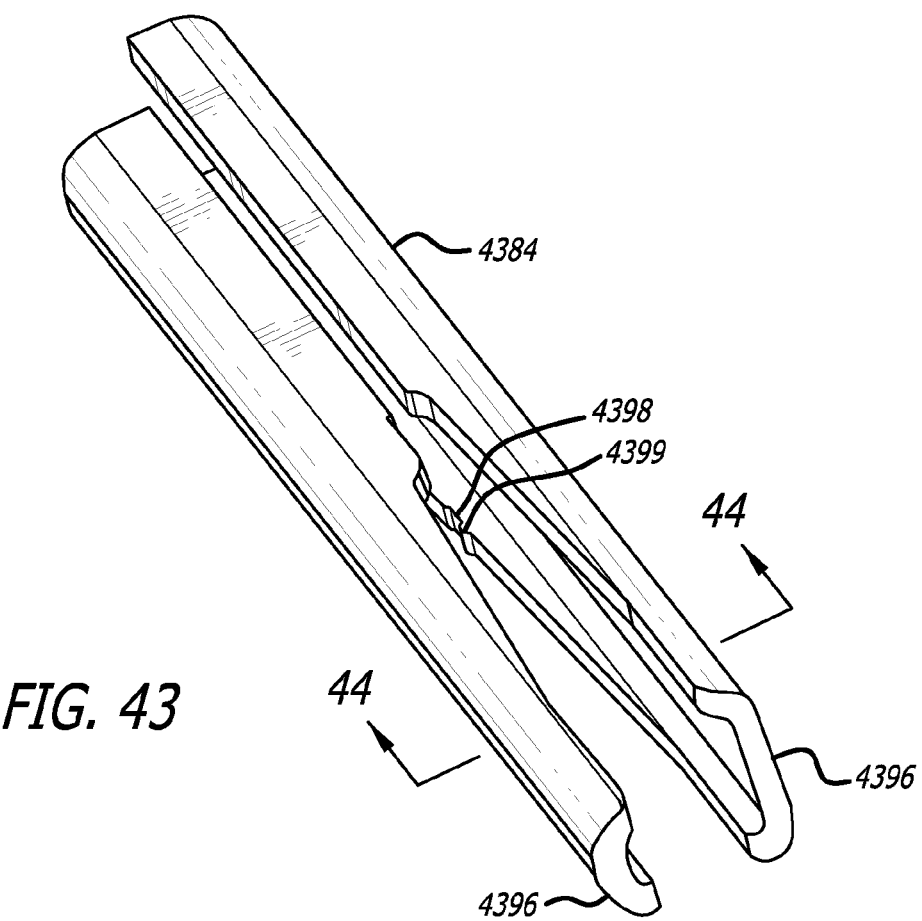
FIG. 43 is a perspective view of a slotted anchor that incorporates a slit along its top and has one prong with a shorter height than the other prong.
Figure 44:
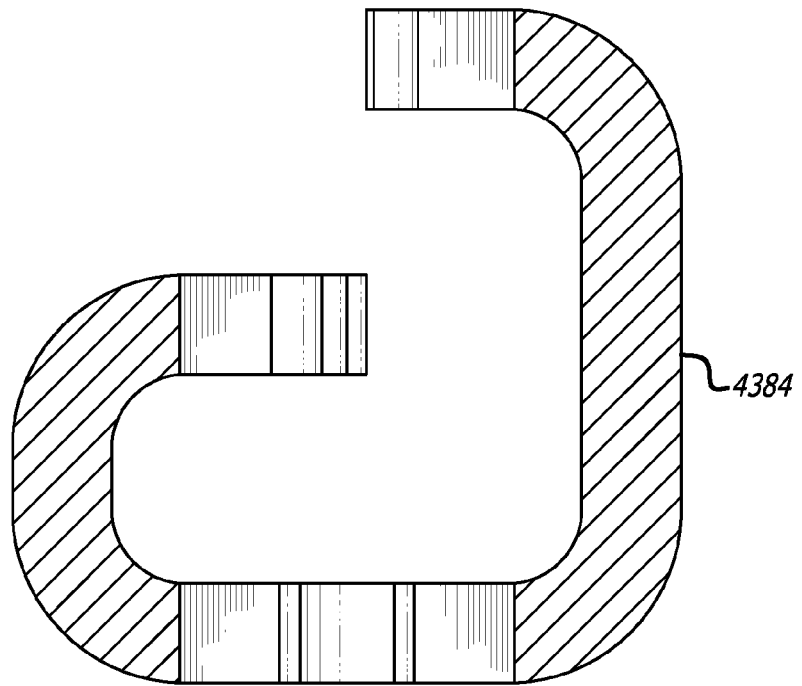
FIG. 44 is a cross-sectional view of the slotted anchor of FIG. 43.
Figure 45:
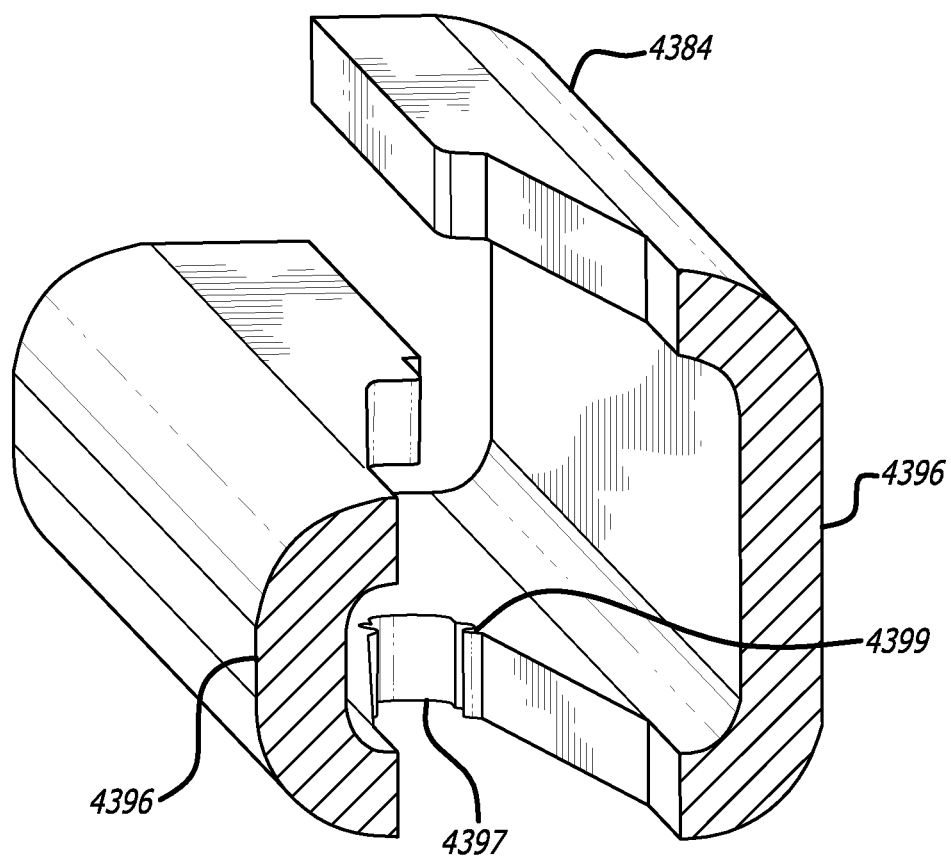
FIG. 45 is a cross-sectional, perspective view of the slotted anchor of FIG. 43.

In yet another embodiment shown in FIGS. 43-45, a slotted anchor 4384 incorporates a slit in its top, and has one prong 4396 with a shorter height than the other prong. In this embodiment, the slotted anchor 4384 includes structure forming tapered prongs 4396 that converge towards inward protrusions 4399 and seating region 4398 formed adjacent the slot inception 4397. This anchor's configuration, which incorporates one prong 4396 with a shorter height than the other prong, creates multiple places at different heights capable of intersecting with a suture 78. In this embodiment, the prongs 4396 generate less distortion of the suture 78, but more friction against the suture.

The disclosed embodiments contemplate both pushing directly on anchor portions of an anchor assembly as well as pushing directly upon the connector of the anchor assembly. Further, an anchor assembly can be delivered and deployed at an interventional site by a deployment device. Consequently, in the context of prostate treatment, the disclosed embodiments accomplish both compressing of the prostate gland and the opening of the prostatic urethra and applying tension between ends of the implant. Moreover, drug delivery is contemplated as a further remedy in BPH and over-active bladder treatment.

Once implanted, the anchor assembly of the disclosed embodiments accomplishes desired tissue approximation, manipulation, compression or retraction, as well as cooperates with the target anatomy to provide an atraumatic support structure. In particular, the shape and contour of the anchor assembly can be configured so that the assembly invaginates within target tissue, such as within natural folds formed in the urethra by the opening of the urethra lumen by the anchor assembly. In fact, in situations where the anchor assembly is properly placed, wispy or pillowy tissue in the area collapses around the anchor structure. Eventually, the natural tissue can grow over the anchor assembly, and new cell growth occurs over time. Such cooperation with target tissue facilitates healing and avoids unwanted side effects such as calcification or infection at the interventional site.

Furthermore, in addition to an intention to cooperate with natural tissue anatomy, the disclosed embodiments also contemplate approaches to accelerate healing or induce scarring. Manners in which healing can be promoted can include employing abrasive materials, textured connectors, biologics and drugs.

It has been observed that placing the anchors at various desired positions within the anatomy can extract the best results. For example, when treating a prostate, one portion of an anchor can be placed within a urethra. It has been found that configuring such anchors so that ten o'clock and two o'clock positions (when looking along the axis of the urethra) are supported or retained, effectively holds the anatomy open and also can facilitate invagination of the anchor portion within natural tissue. This is particularly true in the regions of anatomy near the bladder and the juncture at which the ejaculatory duct connects to the urethra.

Moreover, it is to be recognized that the foregoing procedure is reversible. In one approach, the connection of an anchor assembly can be severed and a proximal (or second) anchor component removed from the patient's body. For example, the physician can simply cut the connector and simultaneously remove the second anchor previously implanted for example, in the patient's urethra. It is to be recognized that various materials are contemplated for manufacturing the disclosed devices. Moreover, one or more components such as distal anchor 70, proximal anchor 84, suture 78, of the one or more anchor assemblies disclosed herein may be designed to be completely or partially biodegradable or bio-fragmentable.

Further, as stated, the systems and methods disclosed herein may be used to treat a variety of pathologies in a variety of tubular structures comprising a cavity or a wall. Examples of such organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, and the like.

Finally, it is to be appreciated that the invention has been described hereabove with reference to certain examples or embodiments, but that various additions, deletions, alterations and modifications may be made to those examples and embodiments without departing from the intended spirit and scope of the disclosed embodiments. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

The various embodiments described above are provided by way of illustration only and should not be construed to limit the disclosed embodiments. Those skilled in the art will readily recognize various modifications and changes that may be made to the disclosed embodiments without following the example embodiments and applications illustrated and described herein, and without departing from the true spirit and scope of the disclosed embodiments, which is set forth in the following claims.

What is claimed:

1. An anchor assembly for applying retractive pressure to tissue, the anchor assembly comprising:
    a distal anchor, wherein the distal anchor includes a head portion that is connected to a tail portion via a connecting mid-section portion, wherein the tail portion is oriented transverse to the head portion;
    a suture, wherein the suture is attachable and tensioned to the distal anchor; and
    a slotted proximal anchor for securing a suture as part of a proximal end of an anchor assembly, the slotted anchor device comprising:
    a tubular back end having a partially flattened cross-section; and
    at least two pairs of spaced apart prongs extending from the back end of the slotted proximal anchor to a front end of the slotted proximal anchor, wherein the pairs of prongs join together at a slot inception, and wherein the prongs are are oriented to receive a tensioned portion of the suture;
    wherein the prongs include inwardly facing protrusions that are configured to capture and deform the suture between the protrusions and prevent the suture from disengaging from the slotted proximal anchor once engaged; and
    wherein inner surfaces of the prongs near the slot inception have a plurality of edges of engagement that deform and compress the suture between the prongs.

2. The anchor assembly of claim 1, wherein the front end of the slotted proximal anchor faces the tensioned portion of the suture.

3. The anchor assembly of claim 1, wherein terminating ends of the prongs are linearly tapered inwardly to facilitate receiving a section of the connector.

4. The anchor assembly of claim 1, wherein the spaced apart prongs commence at a slot inception that steps outwardly to a wider dimension, thereby defining a space between the prongs.

5. The anchor assembly of claim 4, wherein the space between the prongs of the slotted anchor has a dimensional interference, relative to the diameter of the connector.

6. The anchor assembly of claim 1, wherein the inwardly protrusions comprise serrated teeth.

7. The anchor assembly of claim 1, wherein the inwardly facing protrusions comprise barbs.

8. The anchor assembly of claim 1, wherein the inner surfaces of the prongs are configured as corresponding inwardly facing U-shaped prongs, and wherein the inner surfaces of the prongs protrude into the connector.

9. The anchor assembly of claim 1, wherein the prongs have a straight lead-in between terminating ends and a linear taper.

10. The anchor assembly of claim 1, wherein the slotted proximal anchor is formed from a folded member.

11. The anchor assembly of claim 1, wherein the slotted proximal anchor includes a seating portion spaced from the slot inception.

12. The anchor assembly of claim 1, wherein the slot inception includes at least one barb.

13. The anchor assembly of claim 1, wherein the prongs include terminal ends including inwardly directed protrusions.

14. The anchor assembly of claim 1, wherein the prongs include interior planar surfaces leading to internal curved surfaces.

15. The anchor assembly of claim 1, wherein the prongs include interior curved surfaces along their length.

* * * * *